United States Patent

Chiba

[19]

[11] Patent Number: 5,860,912
[45] Date of Patent: *Jan. 19, 1999

[54] STEREOSCOPIC-VISION ENDOSCOPE SYSTEM PROVIDED WITH FUNCTION OF ELECTRICALLY CORRECTING DISTORTION OF IMAGE OR THE LIKE WITH RESPECT TO LEFT- AND RIGHT-HAND IMAGE SIGNALS HAVING PARALLAX, INDEPENDENTLY OF EACH OTHER

[75] Inventor: Masahiro Chiba, Hachioji, Japan

[73] Assignee: Olympus Optical Co., Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 502,845

[22] Filed: Jul. 14, 1995

[30] Foreign Application Priority Data

Jul. 18, 1994 [JP] Japan .................................. 6-165594

[51] Int. Cl.⁶ .................................................. A61B 1/04
[52] U.S. Cl. ............................................. 600/111; 348/45
[58] Field of Search ...................... 348/42, 45; 600/103, 600/111, 128, 136, 166, 181, 109

[56] References Cited

U.S. PATENT DOCUMENTS

| | | | |
|---|---|---|---|
| 4,780,762 | 10/1988 | Nagasaki | 348/235 |
| 4,885,635 | 12/1989 | Kimura et al. | 600/181 X |
| 4,895,431 | 1/1990 | Tsujiuchi et al. | 600/111 X |
| 4,916,534 | 4/1990 | Takahashi et al. | 348/67 |
| 4,987,884 | 1/1991 | Nishioka et al. | 600/181 |
| 5,423,312 | 6/1995 | Siegmund et al. | 600/109 |
| 5,522,789 | 6/1996 | Takahashi | 600/166 |
| 5,588,948 | 12/1996 | Takahashi et al. | 600/111 |

FOREIGN PATENT DOCUMENTS

WO94/13190  6/1994  WIPO .................................. 600/111

*Primary Examiner*—John P. Leubecker
*Attorney, Agent, or Firm*—Armstrong, Westerman, Hattori, McLeland & Naughton

[57] ABSTRACT

Two objective lens systems are disposed at a forward end of an elongated insertion part in spaced relation to the left and right so as to have a parallax in left- and right-hand directions. Images of an object due to respective objective lens systems are image-formed respectively onto CCDs. Image signals which are photoelectrically converted by the respective CCDs are converted into left- and right-hand image signals by a stereo-image-signal processing circuit and are displayed in time division on a monitor. The image signals are observed through left- and right-hand liquid crystal spectacles, whereby it is possible to stereoscopically view the image signals. In order to electrically correct mutual variation due to the two objective lens systems and the two CCDs, distortion which is generated individually, or the like, the image signals of the respective CCDs pass through an image correction circuit which corrects positional shift, inclination, magnification and distortion of an image independently of each other to process correction of the image. A monitor displays the image which is superior in quality.

22 Claims, 18 Drawing Sheets

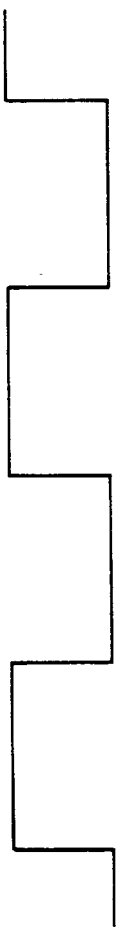
FIG.12A ON/OFF CONTROL SIGNAL
FIG.12B LEFT-HAND EYE SHUTTER
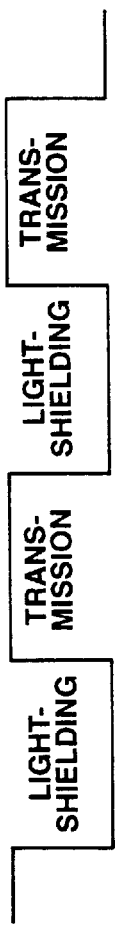
FIG.12C RIGHT-HAND EYE SHUTTER
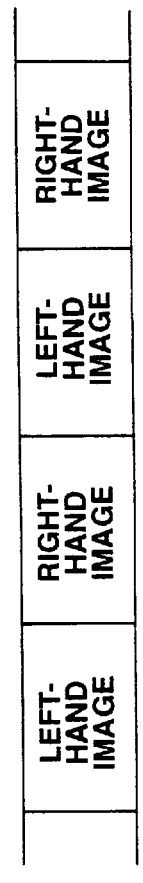
FIG.12D DISPLAY IMAGE

STEREOSCOPIC-VISION ENDOSCOPE SYSTEM PROVIDED WITH FUNCTION OF ELECTRICALLY CORRECTING DISTORTION OF IMAGE OR THE LIKE WITH RESPECT TO LEFT- AND RIGHT-HAND IMAGE SIGNALS HAVING PARALLAX, INDEPENDENTLY OF EACH OTHER

BACKGROUND OF THE INVENTION

1. Field of the Invention

The present invention relates to a stereoscopic-vision endoscope system which can be used for medical treatment and for industry and which electrically corrects distortion of an image with respect to left- and right-hand image signals having a parallax, independently of each other, such that left- and right-hand variations are so dissolved as to be able to practice stereoscopic vision.

2. Description of the Related Art

In recent years, in an endoscope for medical treatment which is used in observation and therapy of, chiefly, the stomach, the large intestine, the bronchus and the like, and, in an endoscope for industry which is used in observation of pipes such as gas pipes, water pipes or the like, and for internal observation of engines or the like, there has been remarkable improvement in image quality. Particularly, various solid-state image pickup elements, such as a charge coupled device (hereinafter, referred to as "CCD"), has advanced miniaturization and produces a high image quality of an electronic endoscope in which the CCD is disposed at a forward end thereof. In keeping therewith, there is a need for increased stero image observation in endoscopes used for medical treatment, where surgical operation is practiced under the endoscope, and, in case, in the endoscope for industry, where the magnitude and the depth of each of flaws, cracks or the like are measured, and the like.

In other fields, stereo observation technique has already been advanced, and it is considered that this technique is applied to the endoscope. As the technique of the stereo observation, a stereoscopic-vision observation system has been developed in which two television cameras are used, two slightly-different images which are generated by a difference in positions of right- and left-hand cameras, that is, a parallax, is acquired to thereby fetch the stereoscopic-view image, and these images are presented on both eyes of a human being, for example, independently of each other, to thereby produce a stereoscopic sense of perspective.

Methods of presenting the stereoscopic-vision image to the human being include a method shown in FIGS. 1A to 3. A method shown in FIGS. 1A–1C is formed such that a monitor 121L for a left-hand eye and a monitor 121R for a right-hand eye are respectively arranged in opposed relation to left- and right-hand eyes 122L and 122R.

In FIG. 1A, for example, the arrangement is such that images on the monitors 121L and 121R are reflected respectively by two mirrors 123L and 124L and 123R and 124R and are seen respectively by left and right eyes 122L and 122R.

The arrangement in FIG. 1B is such that the images on the monitors 121L and 121R are refracted to the left and the right respectively by prisms 125L and 125R and are observed. Further, the arrangement in FIG. 1C is such that the image on the monitor 121L is observed by the left eye 122L, and the image on the monitor 121R is reflected by a mirror 126 and is observed by the right eye 122R.

The arrangement in FIG. 2 is such that polarizing plates 127L and 127R which are set in a perpendicular polarizing direction are arranged respectively in front of display surfaces of the monitors 121L and 121R for the left eye and the right eye, polarizing plates 128L and 128R which are set in the perpendicular polarizing direction are disposed respectively also in front of the left and right eyes 122L and 122R, and the images on the monitors 121L and 121R are seen respectively by the left and right eyes 122L and 122R through a half mirror 129.

FIG. 3 shows that a single monitor 121 is used; and a polarizing member 129 capable of varying the polarizing direction is disposed in front of the monitor 121. The polarizing plates 128L and 128R which are set in the perpendicular polarizing direction are disposed respectively also in front of the left and right eyes 122L and 122R. In the case where left-hand image data of a left-hand-image-data output circuit 130L are displayed on the monitor 121, the polarizing direction of the polarizing member 129 is set to the same direction as the polarizing plate 128L by a left- and right-hand changeover circuit 131; and, in the case where right-hand image data of a right-hand-image-data output circuit 130R are displayed on the monitor 121, the polarizing direction of the polarizing member 129 is set to the same direction as the polarizing plate 128R by the left- and right-hand changeover circuit 131, whereby the left- and right-hand images which are displayed on the single monitor 121 can be observed in separation by the left and right eyes 122L and 122R.

In addition to the above, there is a method of separating images from each other by the use of an electronic shutter.

A prior art example of a stereoscopic-vision system 132 using a single monitor is shown in FIG. 4. A camera 133L for a left-hand image and a camera 133R for a right-hand image respectively photograph images having a parallax between both eyes. The images which are acquired by the left- and right-hand cameras 133L and 133R become digitized image signals, respectively through A/D converters 134L and 134R, and are recorded onto frame memories 135L and 135R. Recording signals thereof are read out alternatively by a double-speed stereo converter 136. Double-speed stereo image signals thereof are converted respectively to analog signals by a D/A converter 137 and are projected onto a double-speed scan monitor 138. Liquid-crystal spectacles 139 are arranged such that left- and right-hand shutters are alternately opened and closed synchronously with the double-speed scan monitor 138.

Accordingly, the left-hand image is seen only by the left eye of an observer, while the right-hand image is seen only by the right eye. Thus, because of the parallax of both eyes, the observer can perceive the image as a stereo image. There is also an arrangement which utilizes polarization in place of the liquid crystal.

Moreover, in order to raise the accuracy of the stereo image, as disclosed, for example, in Japanese Patent Unexamined Publication No. HEI 4-108288 (108288/1992), two television cameras are disposed such that normals of respective image pickup surfaces thereof are parallel to each other, signals are processed such that an interval between image pickup points corresponding respectively to image centers of the two image pickup surfaces is greater than an interval between the centers of two lenses, and lines tying the centers of the lenses and the image pickup points corresponding, respectively, to the image centers to each other are intersected with each other in front of the stereo camera. Since the image pickup surfaces are disposed in parallel to each other, and since the image signals of the two cameras can be shifted in parallel to adequate locations, accurate stereoscopic vision can be practiced which has no distortion.

By the way, the most important matter in the stereoscopic vision which is practiced by the use of the two cameras is that no mutual variation exists between the two cameras. Examples of the variation include image falling-down which occurs when the image pickup surface (CCD surface, for example) of one of the cameras is rotated with respect to a center of an optical axis; inconsistency of the magnitude of the image due to the fact that focal distances of respective lens systems are slightly different from each other and positional shift between the left- and right-hand images due to positional shift of the CCD; distortion of the image due to eccentricity of partial lenses of a lens system and the like.

If the variation occurs mutually, it is impossible to acquire a correct stereo image, and correction is applied by eyes of the observer whereby, if observation is practiced for a long period of time, the observer is liable to be very tired. For this reason, in order to correct the mutual variation, the camera of the prior art example uses a lens barrel which is provided with a CCD position adjustment mechanism and a lens adjustment mechanism, to practice mutual adjustment.

By the way, it is desired for the endoscope to observe a wide range at a time. A minute or microscopic objective lens which has a wide angle-of-view as compared with a general television camera (equal to or more than 60°–140°) and, further, which is disposed at a forward end of an insertion part having a narrow or reduced diameter is used. Accordingly, a variation resulting from working of the lens unit and a variation resulting from assembling of lens parts increase relatively more than in the case where large objective lenses are used.

It is desirable that the forward end of the endoscope is reduced in diameter as much as possible in order to reduce pain resulting from insertion into a patient, or the like. For this reason, the objective lens which is disposed at the forward end must be made as simple a structure as possible. It is difficult to provide a complicated adjustment or regulation mechanism.

In view of the above, an arrangement is proposed in Japanese Patent Unexamined Publication No. HEI 6-59196 (59196/1994) in which shift between left- and right-hand object images is electrically corrected. However, this is arranged such that amounts of shift of the left- and right-hand images are detected from a shift between outlines of the respective images, or the like, and readout addresses of the respective images which are temporality stored in a memory are controlled, or the like, to correct such that both the images coincide with each other.

In this prior art example, a relative amount of shift between the left- and right-hand images is detected to correct such that both the images are coincided with each other, from the amount of shift. Accordingly, principally, correction is carried out such that one of the images is made to coincide with the other image. Thus, in the case where vertical directions of the CCDs are both inclined with respect to a vertical direction of an endoscope body, it is difficult for this prior art example to correct the inclination. Further, also in the case where the magnitudes of the left- and right-hand images are different from each other caused by variations or the like of the left- and right-hand objective lenses, it is impossible to solve this problem by mere correction of the addresses. Similarly, also in the case where distortion of the images due to eccentricity or the like of an optical system is generated on both objective lens systems, correction is carried out on the basis of the relative amount of shift between both the distortions. Accordingly, it is impossible to correct distortion portions which are commonly generated. Thus, there is a problem that it is impossible to acquire a natural stereo image which is arranged so as to faithfully reproduce an object.

Moreover, since there are few degrees of freedom of the layout of the forward end, it is difficult to acquire a parallax which is optimum or adequate to practice stereo observation. What is meant by the optimum parallax means the relation in which inward angles $\Theta$ of the respective two cameras 133L and 133R, for example, satisfy $2°<\Theta<20°$ with respect to an observation object S shown in FIG. 5. If the inward angle $\Theta$ is equal to or less than 2°, a stereo sense or a three-dimensional feeling cannot be acquired.

If the inward angle $\Theta$ exceeds 20°, the left- and right-hand images form double images so that ocellus suppression is generated such that it is impossible to recognize the left- and right-hand images as a single image, and that only a picture on one side is seen. Thus, a deficiency also occurs such that it is impossible to carry out the stereo observation.

In a prior-art general stereo camera, movement means (not shown) is provided so as to be able to set a desired interval between two television cameras, the interval between the cameras is adjusted in accordance with the distance with respect to an observation object, and the inward angle is determined so that a proper parallax is acquired.

In the endoscope, however, it is almost impossible for such movement means to be provided. The interval between the objective lenses corresponding to the two cameras is determined on the basis of the relationship between the inward angle and the distance of the practical range to the observation object. Specifically, the inward angle upon accession increases, while the inward angle upon observation of a great distance decreases. In case of the endsocope for medical treatment, however, it is desired that the interval between two cameras be set such that the inward angle is equal to or less than 20° upon accession or proximity. Assuming that an object distance to the observation object upon accession shown in FIG. 5 is Lnf, and the interval between the two cameras is D, then, the interval D must be set that the following relationship is held:

$$(D/2)\times(1/Lnf)=\tan(\Theta/2)$$

$$D<0.35Lnf \text{ (because of } \Theta<20°)$$

If for example, it is supposed taht the distance Lnf upon accession is 10 mm, the distance D between the two cameras must be made to a value equal to or less than 3.5 mm. Here, whenever a high image quality of the stereoscopic vision is desired, it is necessary to provide multiple picture elements of the CCD so that teh size of the CCD increases. Then, it is necessary to increase the objective lens interval such that an interference of a package of the CCD does not occur. For this reason, it becomes difficult in the endoscope of the prior art example to satisfy the above-described relationship.

SUMMARY OF THE INVENTION

An object or the present invention is to provide a stereoscopic-vision endoscope system which can dissolve mutual variation of an objective lens system without increasing the diameter of a forward end of an endoscope, and in which it is possible to acquire an image for telescopic vision which is suitable for stereo observation and which is superior in quality.

According to the present invention, there is provided a stereoscopic-vision endoscope system comprising:

an endoscope for stereoscopic vision having an elongated insertion part, output means for outputting illumination light for illuminating an object from an illumination window which is provided in a forward end of the insertion part, an objective optical system provided on the forward end of the insertion part, for focusing two images having a parallax with respect to the object which is illuminated by the illumination light, and two image pickup elements for photoelectrically converting the two images at least on the basis of the objective optical system;

image-signal conversion means for converting two image signals photoelectrically converted by the two image pickup elements to a stereo image signal so as to be able to be viewed stereoscopically;

display means for displaying the stereo image signal so it is recognizable by an observer as a stereoscopic image; and image correction means for electrically correcting optionally at least one of magnitude, distortion, inclination and positional shift of the image, independently of each other, with respect to the two image signals corresponding respectively to the two images of the stereo image signal.

Thus, even when there is distortion or the like, the respective objective optical systems which are disposed at the forward end can be corrected such that the image more faithfully represents the object, and the variation of the left- and right-hand images, or the like, can also be eliminated. Accordingly, it is possible to display a stereoscopic vision image which is superior in quality, and which is suited for stereo observation, on the display means.

BRIEF DESCRIPTION OF THE DRAWINGS

FIGS. 6 to 15B relate to a first embodiment of the present invention, FIG. 6 being an entire arrangement view of a stereoscopic-vision endoscope system according to the first embodiment;

FIG. 7 is a block diagram showing an arrangement of a signal processing system of the stereoscopic vision in FIG. 6;

FIG. 8 is a block diagram showing a more detailed arrangement of the signal processing system in FIG. 7;

FIG. 9 is a block diagram showing an arrangement of an image correction circuit;

FIG. 10 is a cross-sectional view showing a detailed structure example of an image pickup optical system at a forward end of an insertion part;

FIGS. 12A to 12D are explanatory views of an operation which displays left- and right-hand images on a stereo-image display monitor;

FIG. 14 is an explanatory view showing a setting example for image correction;

FIG. 15B is an explanatory view in which an image before correction of distortion is displayed on the monitor;

FIG. 20 is a cross-sectional view showing a specific structure of the image pickup optical system at the forward end in FIG. 19;

FIG. 22 is a cross-sectional view showing a specific structure of the image pickup optical system at the forward end in FIG. 21;

FIG. 25B is a cross-sectional view taken along a line A–A' in FIG. 25A;

FIG. 26B is a cross-sectional view taken along a line B–B' in FIG. 26A.

DESCRIPTION OF THE PREFERRED EMBODIMENTS

Embodiments of the invention will hereunder be described in detail with reference to the accompanying drawings.

Figure 6:
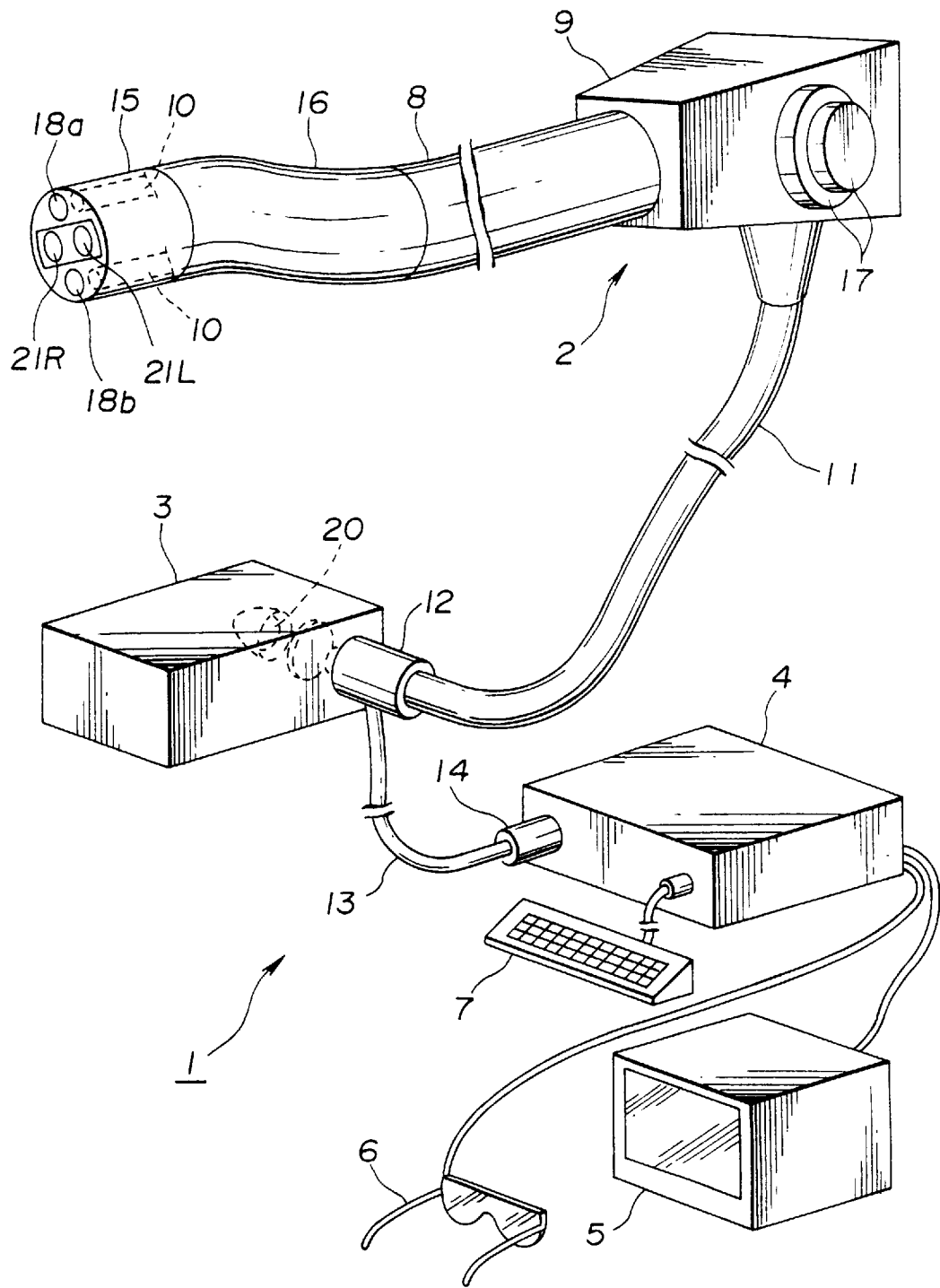

A stereoscopic-vision endoscope system I according to a first embodiment of the invention, shown in FIG. 6, comprises an electronic endoscope 2 for stereoscopic vision, provided with a function of stereo image pickup, a light source device 3 for supplying illumination light to the electronic endoscope 2 for stereoscopic vision, a stereo-image processing device 4 for carrying out signal processing with respect to image pickup means for stereoscopic vision, which is built in the electronic endoscope 2 for stereoscopic vision to carry out the stereo image pickup, a display monitor 5 for stereoscopic vision, for displaying an image signal for stereoscopic vision (also referred to as "stereo image signal") to be stereoscopically viewed, which is outputted from the stereoimage processing device 4, spectacles 6 for stereoscopic vision, which are used by a user who stereoscopically views left- and right-hand images which are displayed on the display monitor 5 for stereoscopic vision, and a keyboard 7 for inputting an image correction amount, characters or the like.

The electronic endoscope 2 for stereoscopic vision comprises an insertion part 8 which is elongated and which has an elasticity so as to be capable of being inserted into a bent body cavity or the like, an operation part 9 having a great width formed at a distal end of the insertion part 8, for practicing operations such as grasping, curvature or the like, a universal cable 11 extending from the operation part 9 to the exterior, a light guide connector 12 provided at a distal end of the universal cable 11, a signal cable 13 extending from the side of the light guide connector 12, and a signal connector 14 provided at a distal end of the signal cable 13.

A bendable curvature part 16 is formed adjacent to a forward end 15 of the insertion part 8. The curvature part 16 is angularly moved by operation of a curvature operation knob 17 which is provided on the operation part 9, to thereby be able to curve the curvature operation knob 17 in optional directions including the upper and bottom and the left and right.

Two light guides 10, 10 are inserted into the insertion part 8. These light guides 10, 10 are brought together within the operation part 9. The light guides 10, 10 are further inserted into the universal cable 11.

Ends of the respective light guides reach the light guide connector 12.

The light guide connector 12 is connected to the light source device 3, whereby illumination light of a lamp 20 within the light source device 3 is converged by a lens and is supplied to an end surface of the light guide. The supplied illumination light is transmitted by the light guide which serves as illumination-light transmission means, and is outputted from illumination-light output means on the forward end of the insertion part 8. That is, distal ends of the two light guides 10, 10 within the insertion part 8 are fixed to the forward end 15. The illumination light which is outputted from each end surface passes through illumination lenses 18a and 18b which are mounted on an illumination window opposed against each end surface, and is outputted forwardly, to illuminate an object such as a diseased or affected part or the like.

Figure 7:
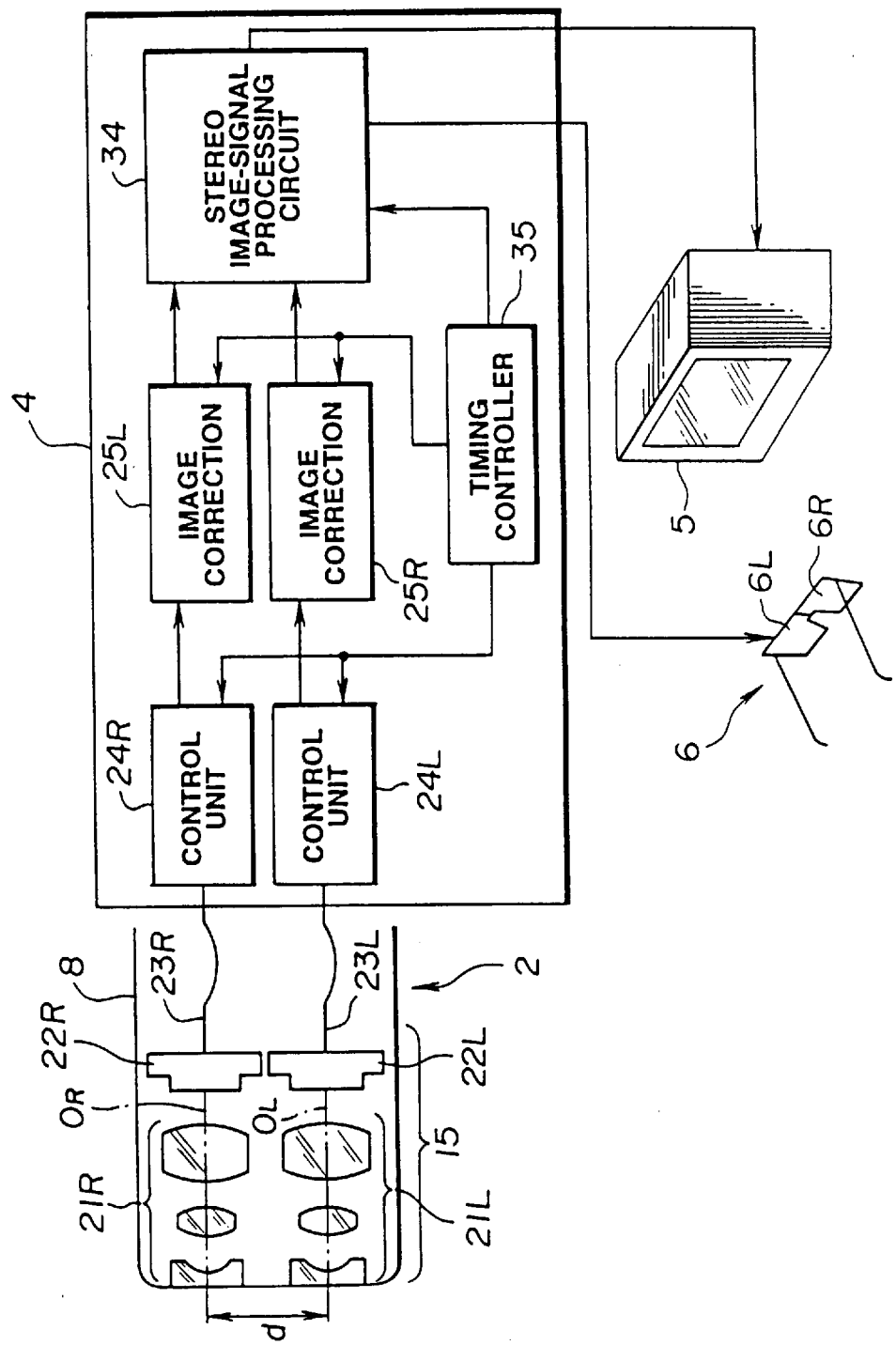

Two view windows are formed in the forward end 15 adjacent to the illumination lenses 18a and 18b, which serve as an illumination optical system. Objective lens systems 21L and 21R are mounted respectively on the view windows. As shown in FIG. 7, two image pickup elements provided respectively with photoelectric conversion functions, for example, CCDs 22L and 22R, are disposed respectively at image-formation positions of the respective objective lens systems 21L and 21R.

The above-described pair of objective lens systems 21L and 21R are disposed respectively on both sides of a center axis of the insertion part 8, for example, on both sides in left- and right-hand directions or a horizontal direction such that a distance between optical axes OL and OR is d, for example. In other words, the optical axes OL and OR are spaced apart by an amount d. Thus, left- and right-hand object images (referred simply also to as "left- and right-hand images") having a parallax in the left- and right-hand directions with respect to a forward object are focused onto respective photoelectric conversion surfaces (image pickup surfaces) of the respective CCDs 22L and 22R.

Output signals (image pickup signals which are photoelectrically converted, corresponding respectively to the left- and right-hand images) which are outputted respectively from the two CCDs 22L and 22R pass respectively through signal cables 23L and 23R, and are inputted respectively into control units 24L and 24R. Thus, output signals from the CCDs 22L and 22R are converted to an image signal for displaying the output signals from the CCDs 22L and 22R on a display means.

In the image signals which are acquired respectively by the control units 24L and 24R, there are many cases where left- and right-hand images are not coincident with each other even when photographed so as to be originally coincident with each other (an object under an equivalent state with respect to left- and right-hand image pickup optical systems, for example) which is caused by distortion or variation in every unit of each of the objective lens systems 21L and 21R and positional shift and inclination of the CCDs 22L and 22R.

Two image correction circuits 25L and 25R are provided for the respective image signals such that an image which faithfully reflects the object can be generated and variation or the like of the left- and right-hand images (with respect to the same object) can be eliminated and displayed. The image correction circuits 25L and 25R electrically correct magnification, distortion, positional shift and inclination with respect to each of the image signals. Thereafter, the image correction circuits 25L and 25R output the image signals to the monitor 5 which serves as a display means, through a stereo image-signal processing circuit 34, to improve the quality of each of the images which are displayed on the monitor 5 so that an image which is suitable for the stereoscopic vision can be displayed.

Figure 8:
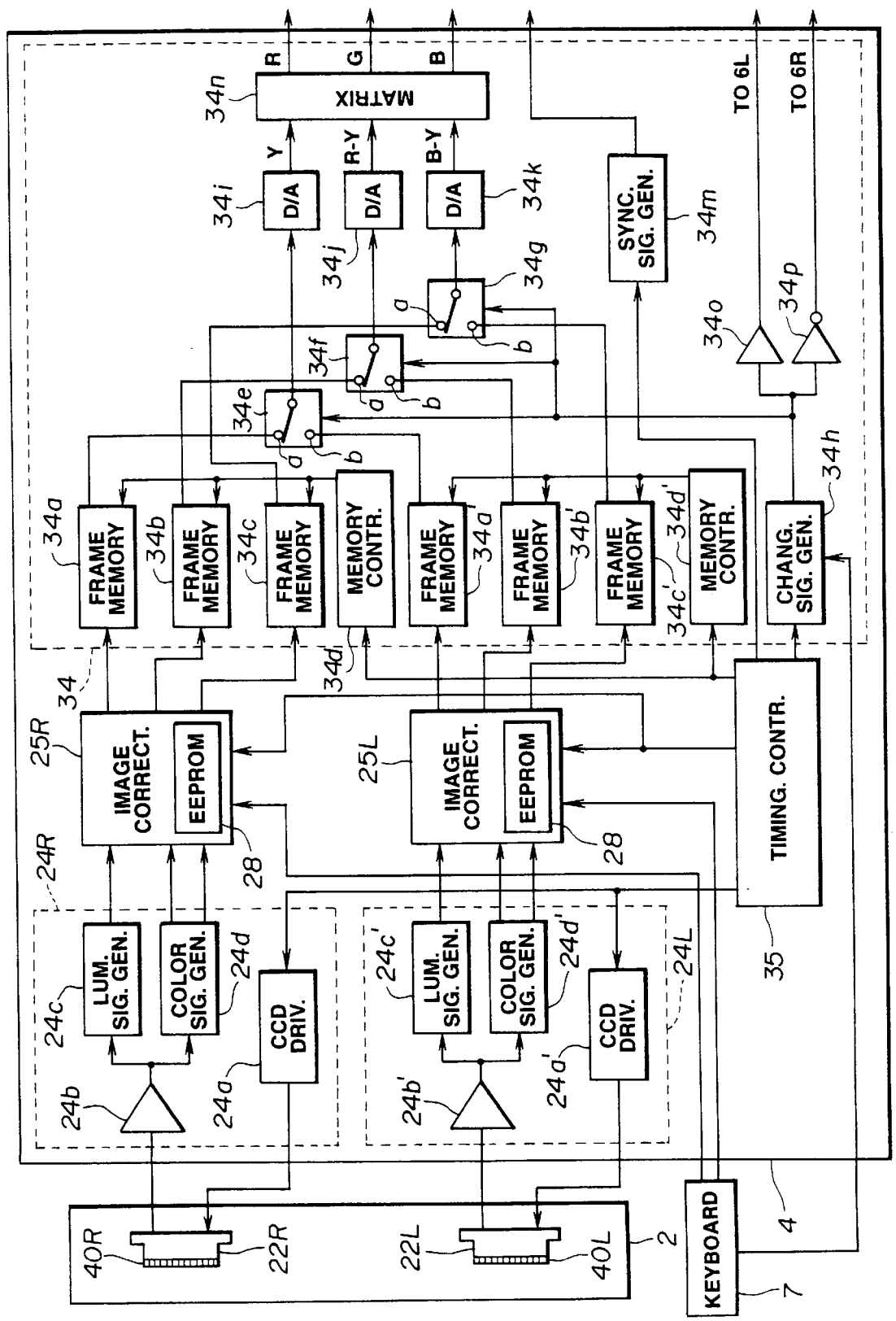

FIG. 8 shows an entire arrangement of the signal processing system. A CCD drive signal which is outputted from a CCD driver 24a within the control unit 24R is applied to the CCD 22R so that an electrical signal which is photoelectrically converted, corresponding to the image is outputted. This signal is amplified by an amplifier 24b and, thereafter, is inputted to a luminance-signal generation circuit 24c and a color-signal generation circuit 24d. Thus, a luminance signal Y and color-different signals R-Y and B-Y are generated, and are outputted to the image correction circuit 25R.

By the image correction circuit 25R, the magnitude, the inclination, the distortion and the positional shift of the right-hand image are electrically corrected and, thereafter, are outputted to the stereo image-signal processing circuit 34.

Similarly, the CCD drive signal which is outputted from a CCD driver 24a' within the control unit 24L is applied to the CCD 22L so that an electric signal which is photoelectrically converted, corresponding to the image is outputted. The signal is amplified by an amplifier 24b' and, thereafter, is inputted to a luminance-signal generation circuit 24c' and a color-signal generation circuit 24d'. Thus, the luminance signal Y and the color different signals R-Y and B-Y are generated, and are outputted to the image correction circuit 25L By the image correction circuit 25L, the magnitude, the inclination, the distortion and the positional shift of the left-hand image are electrically corrected and, thereafter, are outputted to the stereo image-signal processing circuit 25L.

By the image correction circuit 25L, the magnitude, the inclination, the distortion and the positional shift of the left-hand image are electrically corrected and, thereafter, are outputted to the stereo image-signal processing circuit 34.

The luminance signal Y and the color-difference signals R-Y and B-Y corresponding to the right-hand image, which are inputted to the stereo image-signal processing circuit 34 are respectively stored temporarily in frame memories 34a, 34b and 34c under the control of a memory controller 34d.

Similarly, the luminance signal Y and the color dItterence signals R-Y and B-Y corresponding to the left-hand image, which are inputted to the stereo image-signal processing circuit 34 are respectively stored temporarily in frame memories 34a', 34b' and 34c' under the control of a memory controller 34d'.

Each of the frame memories 34a, 34b, 34c, 34a', 34b' and 34c' is a pair of image memories which have a memory capacity corresponding to a single frame (that is, the capacity capable of storing one image). An image which is stored in one memory can be read out while writing is carried out on the other memory.

The memory controller 34d stores the luminance signal Y and the color-difference signals R-Y and B-Y which are inputted during a normal frame period (that is, ⅓₀S), to the frame memories 34a, 34b and 34c. When the memory controller 34d reads out the stored image, the memory controller 34d reads out the stored image at twice the speed. Specifically, the memory controller 34d reads out the images which are stored in the frame memories 34a, 34b and 34c, during a ½ frame period.

Similarly, the memory controller 34d' stores the luminance signal Y and the color-difference signals R-Y and B-Y which are inputted during a normal frame period (that is, ⅓₀S), to the frame memories 34a', 34b' and 34c'. When the memory controller 34d' reads out the stored image, the memory controller 34' reads out the stored image at twice the speed. Specifically, the memory controller 34d' reads out the images which are stored in the frame memories 34a', 34b' and 34c', during a ½ frame period.

The signals which are read out from the frame memories 34a, 34b and 34c and the frame memories 34a', 34b' and 34c' are such that signals corresponding to the left- and right-hand images are alternately selected respectively by changeover switches 34e, 34f and 34g. That is, a changeover-signal generation circuit 34h generates a changeover signal of one frame period which alternate between "H" and "L" with a 50% duty cycle, by a timing signal from a timing controller 35. The changeover-signal generation circuit 34h alternately changes over the changeover switches 34e, 34f and 34g by the changeover signal, to alternately select contacts a and b. The signal on the selected side is converted to the analogous luminance signal Y and the analogous color-difference signals R-Y and B-Y by D/A converters 34i, 34j and 34k.

Further, the timing signal from the timing controller 35 is inputted to a synchronous-signal generation circuit 34m. Thus, a double-speed synchronous signal (that is, a period ½ of normal) is generated.

The analogous luminance signal Y and the analogous color-difference signals R-Y and B-Y are converted to chrome signals of R, G and B by a matrix circuit 34n, and are outputted to the monitor 5 for stereoscopic vision together with the synchronous signal S. The left- and right-hand images are alternately displayed in color by the monitor 5.

The changeover signals come into ON/OFF control signals through a buffer 34o and an inversion buffer 34p, and are applied to the crystal shutters 6L and 6R for the left- and right-hand eyes of the spectacles 6 for stereoscopic vision. By the application of the ON/OFF control signals, the liquid crystal shutters 6L and 6R for the left and right eyes are alternately set to transparent and light-shielding states in synchronism with the display period of the left- and right-hand images which are alternately displayed on the monitor 5. Thus, an observer who observes the monitor 5 which uses the spectacles 6 for stereoscopic vision can stereoscopically recognize it from the left- and right-hand images having parallax.

The keyboard 7 is connected to the image correction circuits 25L and 25R. By the command inputting and the data inputting from the keyboard 7, the image correction circuits 25L and 25R correct distortion of the images or the like to the left and the right independently of each other. Moreover, information on the correction, that is, the respective correction coefficient values of the positional shift, the inclination, the size and the distortion are stored respectively in EEPROMs 28 which are provided respectively within the image correction circuits 25L and 25R. Processing of the image correction is practiced with reference to the information which is stored in the EEPROMs 28.

Furthermore, the keyboard 7 is connected to the changeover-signal generation circuit 34h. A manual changeover command is sent from the keyboard 7, whereby the changeover signal from the changeover-signal generation circuit 34h can be controlled manually. For example, whenever the distortion of the image is corrected by the left or the right, only the image signal which corresponds to the image which is corrected is always outputted to the side of the monitor 5, and the ON/OFF control signal is set such that only the image which corrects the spectacles 6 for stereoscopic vision can be observed.

Figure 9:
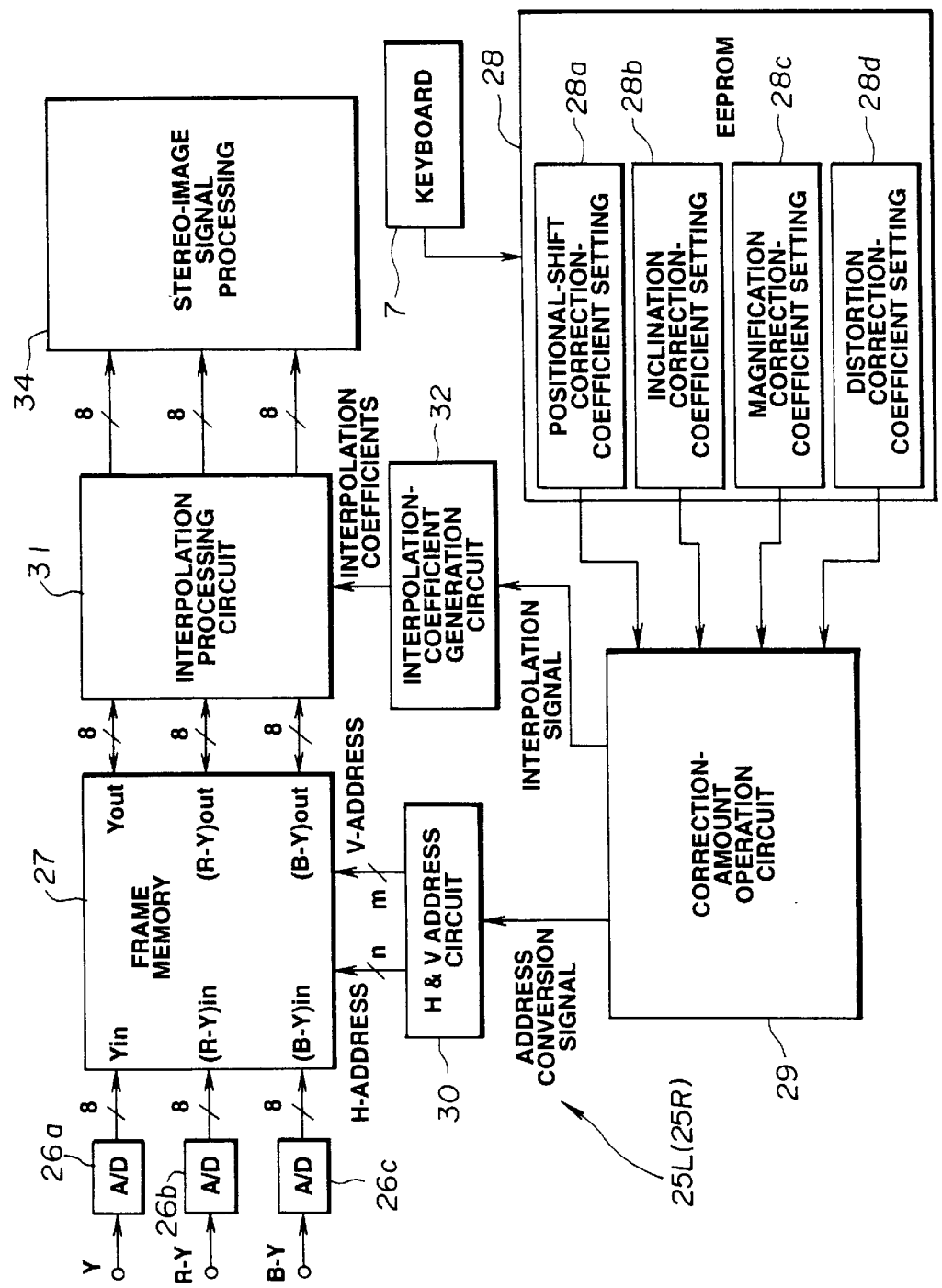

FIG. 9 shows a block diagram of the image correction circuit 25L or 25R. The image signal which is outputted from the CCD 22L or 22R and which is generated by the control unit 24L or 24R, that is, the luminance signal Y and the color-difference signals R-Y and B-Y which serve as lumlnance/color-separation signals, for example, are inputted to A/D converters 26a, 26b and 26c and are A/D converted thereby respectively. The luminance signa Y and the color-difference R-Y and B-Y come into digital signal data Yin, (R-Y)in and (B-Y)in of 8 bits, for example, which are written into a frame memory 27 from respective input ends of the frame memory 27.

The frame memory 27 has three sets of image memories for Y, R-Y and B-Y, which have memory cells with the number of picture elements being slightly greater than the number of picture elements of the CCD 22L or 22R. Each set consists of a plurality of image memories. Thus, the frame memory 27 is arranged such that the image signal data which are generated by the control unit 24L or 24R and which are A/D-converted are stored in a single image memory for each of the sets, and an image where four kinds of correction are carried out, including the positional shift, the inclination, the magnitude and the strain or distortion of the image, can be stored in another image memory.

The image signal which is read out from the CCD 22L or 22R is once stored in a center part of the image memory which forms the frame memory 27.

The address signal which is read out is shifted (altered or modified), whereby the shift in the vertical (longitudinal) and left- and right-hand (lateral) directions can easily be corrected. Whenever the read-out timing is shifted, the frame memory 27 may be an image memory which have the number of memory cells the same as the number of picture elements of the CCD 22L or 22R.

Reading-out from the frame memory 27 is as follows: The respective correction coefficient values from a positional-shift correction-coefficient setting circuit 28a, an inclination correction-coefficient setting circuit 28b, a magnification correction-coefficient setting circuit 28c and a distortion correction-coefficient setting circuit 28d which set respective correction coefficient values for the positional shift, the amount of rotation (the inclination), the magnification (the magnitude of the image), and the distortion are inputted to a correction-amount operation circuit 29. The correction-amount operation circuit 29 performs correction processing referring to these correction-coefficient values. By the operation, the correction-amount operation circuit 29 outputs address conversion signals corresponding respectively to the correction coefficient values, to a horizontal & vertical address circuit (hereinafter referred to as "H & V address circuit") 30, and outputs an interpolation signal to an interpolation-coefficient generation circuit 32.

Respective correction-coefficient setting circuits 28a–28d are formed by the EEPROM 28 which serves as non-volatile memory means which can electrically reload the data, or the like, for example. The EEPROM 28 is connected to the keyboard 7, and stores the correction-coefficient values from the keyboard 7 into memory regions which correspond respectively to the circuits 28a–28d.

The H & V address circuit 30 generates an H address of n bits and a V address of m bits, for example, such that the positional shift, the inclination, the magnification and the distortion are corrected with respect to the data which are written to the frame memory 27, to thereby correct the readout data of the frame memory 27.

Output data Yout, (R-Y)out and (B Y Y)out which are read out and outputted by the frame memory Z7 are inputted to an interpolation processing circuit 31, and processing such as interpolation or the like between picture elements is practiced by the interpolation processing circuit 31. The correction-amount operation circuit 29 generates an interpolation signal for prescribing interpolation coefficients on the basis of the respective coefficient values which come into the correction information of the left- and right-hand and the upper and lower positional shift, inclination, magnification and distortion which are inputted to the correction-amount operation circuit 29, and outputs the same to the Interpolation-coefficient generation circuit 32.

The interpolation-coefficient generation circuit 32 generates the interpolation coefficients on the basis of the inputted interpolation signal, and outputs the same to the interpolation processing circuit 31. The interpolation processing circuit 31 performs interpolation and smoothing processing (including correction) by the use of the interpolation coefficients with respect to the data which are read out by the frame memory 27. The image signal data which are corrected as discussed above are supplied to the stereo image-signal processing circuit 34.

In connection with the above, the correction-ended image-signal data in which the correction of all the four kinds have been carried out are outputted to the stereo imagesignal processing circuit 34. However, the image-signal data on the way of correction are stored temporality in the image memory within the frame memory 27. For example, correction of the positional shift is first carried out with respect to the image signal data before correction, as described subsequently. The corrected image-signal data are stored in an image memory (hereinafter referred to as "first image memory") within the frame memory 27. The inclination correction is practiced with respect to the image signal data which are stored in the first image memory in which the positional shift is corrected. After the correction of the inclination, correction of the magnitude and correction of the distortion are successively carried out. The image signal data in which all four kinds of correction are performed are outputted to the stereo image-signal processing circuit 34.

The correction-amount operation circuit 29 is formed by the use of a CPU and which operates or calculates, in real time, input conditions, the positional shift, the inclination, the magnification and the distortion. Further, if the input conditions which are previously corrected are determined, the circuit is not limited to one which is formed by the use of the CPU, but which may by formed by fixed data due to a ROM.

These corrected left- and right-hand image signals (corresponding respectively to the left- and right-hand images) are converted to a stereo image signal such as to be able to be stereoscopically viewed (in the present embodiment, a signal in which the left- and right-hand image signals are alternately outputted in time sharing or time division) by the stereo image-signal processing circuit 34, and are displayed on the stereo image display monitor 5.

The control units 24L and 24R, the image correction circuits 25L and 25R and the stereo image-signal processing circuit 34 carry out signal processing in synchronism with a synchronous signal from the timing controller 35. Moreover, the timing controller 35 sends the ON/OFF control signal with respect to the liquid crystal shutters 6L and for the spectacles 6 for stereoscopic vision, and is turned ON/OFF (is transparentized/is light-shielded) in synchronism with the left- and right-hand display images which are displayed in time sharing on the stereo image display monitor 4 so that the left- and right- hand images can be observed respectively by the left and right eyes.

Figure 10:
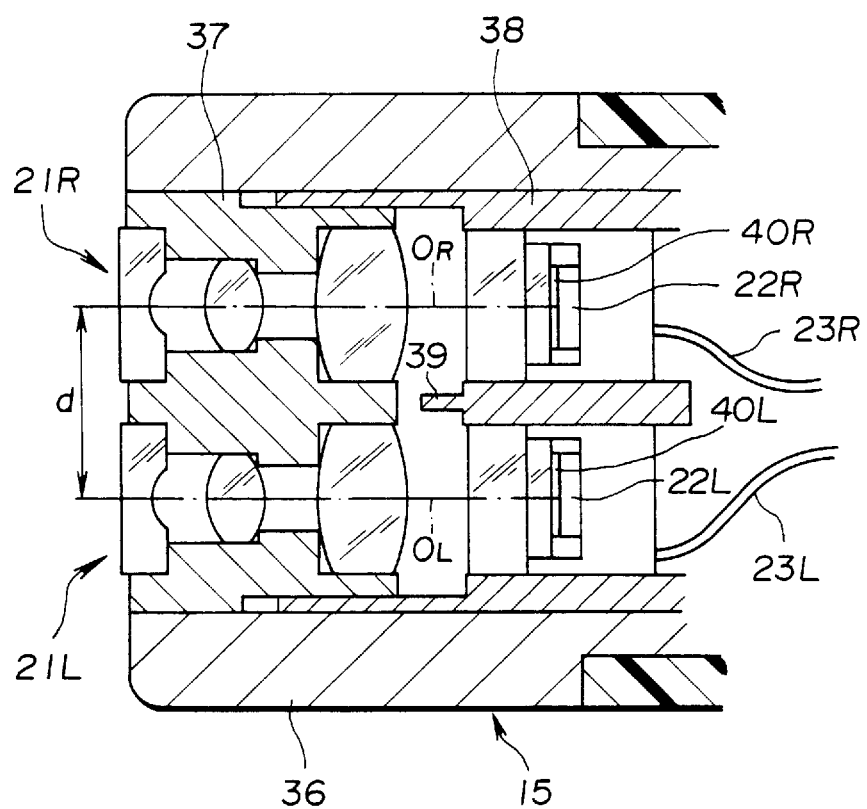

FIG. 10 shows an example of the detailed layout of the forward end 15 in FIG. 7. An objective lens unit 37 is fitted in a transparent bore or a through-bore which is provided in a forward-end member 36 which forms the forward end 15. Two objective lens systems 21L and 21R are integrally mounted on the objective lens unit 37. Furthermore, a CCD unit 38 which has a proximal end side thereof which is fitted in a distal end side of the objective lens unit 37 is fitted in the through-bore. The CCDs 22L and 22R are integrally mounted on the CCD unit 38.

Figure 11A:
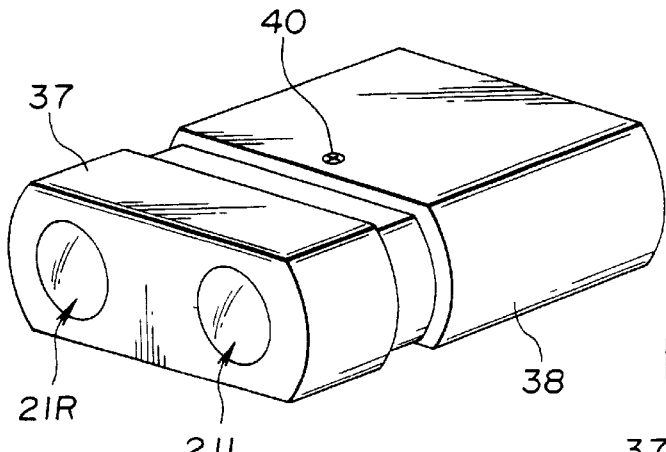
FIG. 11A is a perspective view showing a form of an objective lens unit and a CCD unit.
Figure 11B:
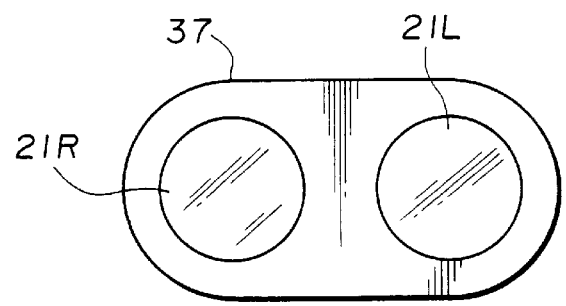
FIG. 11B is a front elevational view of the objective lens unit and the CCD unit.

As shown in FIG. 11A, an interval between the objective lens unit 37 and the CCD unit 38 which are fitted in each other is adjusted whereby focus adjustment is carried out once with respect to the left- and right-hand image pickup optical systems. After the focus adjustment, the objective lens unit 37 and the CCD unit 38 are fixed to the forward-end member 36 by a fixing screw 40 or an adhesive. In this connection, FIG. 11B is a front elevational view of FIG. 11A.

In connection with the above, as shown in FIG. 10, the CCD unit 38 is formed with a projection 39 which projects forwardly between the CCDs 22L and 22R which are disposed adjacent thereto, so that light which passes through the side of the objective lens system 21L (21R) is not leaked to the side of the CCD 22R (22L). Mosaic filters 40R and 40L are mounted respectively just in front of photoelectrically conversion surfaces of CCD chips of the respective CCDs 22R and 22L. Color separation is optically performed just before the photoelectrically conversion surface, to R, G, B and the like every each picture element. Glass materials are provided respectively in front of the mosaic filters 40R and 40L to protect the interior thereof.

Function of the present embodiment will subsequently be described.

First, the left- and right-hand images are displayed in a time-sharing fashion on the monitor 4. Stereoscopic viewing by the spectacles 6 for stereoscopic vision will be described with reference to FIGS. 12A to 12D.

The timing controller 35 sends the ON/OFF control signal shown in FIG. 12A to the spectacles 6 for stereoscopic vision. The liquid crystal shutters 6L and 6R alternate between the transparent and light-shielding states, as shown in FIGS. 12B and 12C. Meanwhile, the left- and right-hand images are alternately displayed on the monitor 4, as shown in FIG. 12D, in synchronism with the ON/OFF control signal. Accordingly, the operator which has the spectacles 6 for stereoscopic vision, or the like, always observes the left-hand image by the left eye and the right-hand image by the right eye. Thus, the operator can practice stereoscopic vision.

Function of the image correction due to the image correction circuits 25L and 25R will subsequently be described. The reference object in which a reference line is drawn in the form of a square lattice is installed at a position which is spaced so as to be regarded as existing on optical axes OL and OR of the respective objective lens systems 21L and 21R, in opposed relation to the forward end 15 of the electronic endoscope 2, for example. An image of the object is displayed on the monitor 5.

Figure 13A:
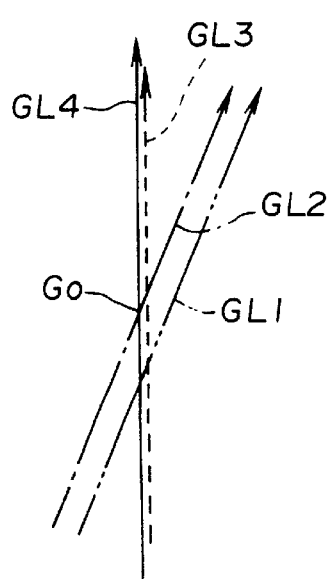
FIGS. 13A and 13B are explanatory views of a summary operation of the image correction circuit.
Figure 13B:
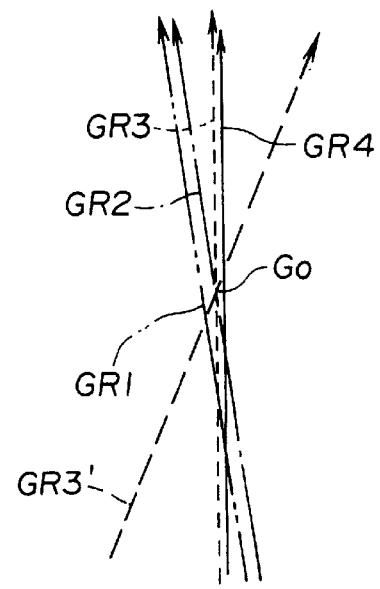

Summary of the function of the image correction due to the image correction circuits 25L and 25R, with respect to the image of the object, is shown in FIGS. 13A and 13B.

It is supposed that, with regard to an object 45, the left- and right-hand images before correction is practiced by the image correction circuits 25L and 25R are images GL1 and GR1 shown by two-dot-and-chain lines, with respect to the center position Go of the image display range of the monitor 5 (it is supposed that, for simplification in FIGS. 13A and 13B, the images are shown respectively by the images GL1 and GR1 with respect to case where the object is an arrow which is vertically set on the optical axis and, further, a center position of the length of the arrow is located on the optical axis). Then, the correction coefficient values which correct the respective shift amounts of the image correction circuits 25L and 25R are inputted from the keyboard 7, and the correction coefficient values of the shift amount in the horizontal direction, for example, are set by the positional-shift correction coefficient setting circuit 28*a*.

Specifically, the correction coefficient values with respect to the respective images GL1 and GRI are inputted from the keyboard 7, whereby the positional-shift amount correction coefficient value is set in the positional-shift correction-coefficient setting circuit 28*a*. The correction-amount operation circuit 29 corrects the positional-shift amount on the basis of the set positional-shift-amount correction coefficient value. By this operation, the address conversion signal to practice modification of the address and the interpolation signal for practicing the interpolation are computed, and are outputted to the H & V address circuit 30 and the interpolation coefficient generation circuit 32.

The address which is read out from the frame memory 27 is modified by the address conversion signal. The positional shift is corrected in unit of the picture element by the modification of the address. The image signal data which are read out from the frame memory 27 are further interpolated by the,interpolation processing circuit 31 by the use of the interpolation coefficients which are generated by the interpolation-coefficient generation circuit 32. Thus, correction of the finer positional shift is carried out.

Whenever the signal in which the positional shift is corrected is displayed on the monitor 5, an image thereof can be set to left- and right-hand images GL2 and GR2 which are shown by one-dot-and-chain lines, and can be corrected to an image under a condition that there is no positional shift in the horizontal direction (under a condition that center positions of the respective images GL2 and GR2 are not shifted in the horizontal direction). In this manner, the correction coefficient values corresponding respectively to the images GL1 and GR1 are inputted with respect to the images GL1 and GR1 having respective positional shift amounts thereof different from each other, whereby, like the images GL2 and GR2 shown by the one-dot-and-chain lines, respective positional shifts are dissolved. Thus, the images GL2 and GR2 can be set so as to be displayed under a condition as to be positioned at the center position Go. By codes of the correction coefficient values, it is also possible to cope with a shift in position in the opposite direction.

The correction coefficient values of the inclination amount are set by the inclination correction coefficient setting circuit 28*b* with respect to left- and right-hand images GL2 and GR2 shown by the one-dot-and-chain lines, whereby it is possible to set the image which is displayed on the monitor 5, to left- and right-hand images GL3 and GR3 shown by broken lines. Also in this case, the inclination-amount correction-coefficient value is set from the keyboard 7 so as to correct the inclination amounts of the respective images GL2 and GR2. Correction processing is carried out on the basis of the inclination-amount correction-coefficient value, whereby the image can be made to an image in which the inclination is dissolved. In the case of being displayed on the monitor 5, the image can be set to the images GL3 and GR3 which are exactly oriented toward the upper direction and the lower direction.

It is supposed that there is only one image correction circuit 25R. Then, since only the side of one image GR2 can be corrected (here, the inclination amount can be corrected), setting must be made to a state which is larger in inclination (an image shown by GR3' in FIG. 13B), in order to correct variation with respect to the other image GL2. To the contrary, in the present embodiment, since the respective image signals are corrected to produce an image state which faithfully reproduces the object, setting can be made to a state in which the image quality is superior (here, there is no inclination). Moreover, setting can be made to a state in which mutual variation can also be dissolved.

Furthermore, the correction coefficient value of the magnification is set by the magnification correction coefficient setting circuit 28*c*, whereby the magnitudes of the respective images GL3 and GR3 can be enlarged or reduced. The correction coefficient values are set respectively with respect to the images GL3 and GR3 so as to become the desired magnitude, whereby it is possible to set the images which are displayed on the monitor 5, to images which are equal in magnitude to each other like left- and right-hand images GL4 and GR4 shown by the solid lines.

Further, the correction coefficient value of the distortion amount including various kinds of aberrations such as bending, etc., is set by the distortion-coefficient setting circuit 28d whereby it is possible to set the image to an image which has substantially no distortion (including the meaning of the various kinds of aberrations).

In connection with the above, the correction of the shift amount has been described with reference to the horizontal direction for simplification. However, the shift amount in the upper and lower direction (the vertical direction) can also be corrected similarly.

The image correction function will subsequently be described in a more detailed manner.

Figure 14:
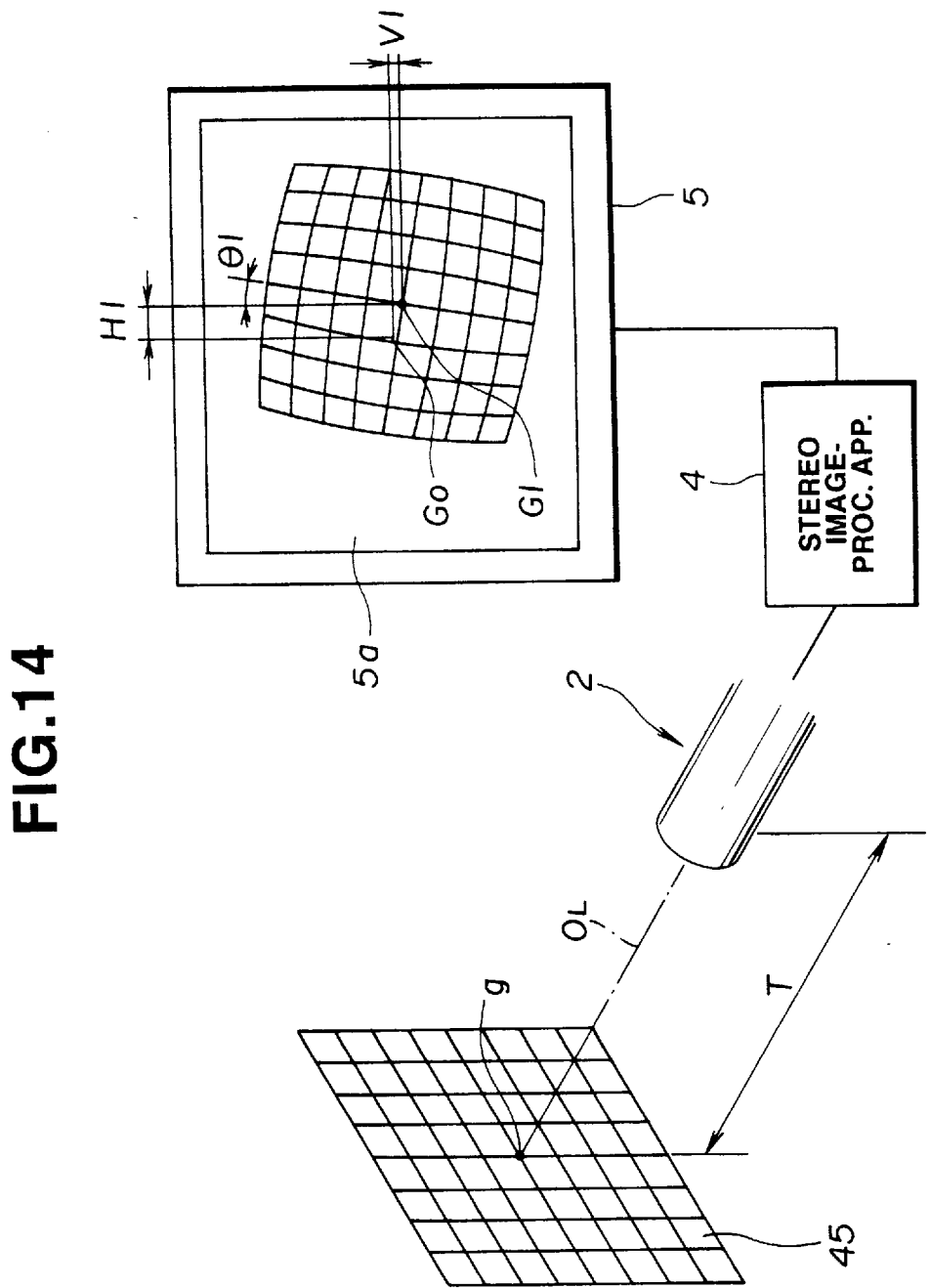

The reference object 45 in which the reference line is drawn in the form of the square lattice is installed at a position which is spaced a predetermined distance T on the optical axis OL of the objective lens system 21L, in opposed relation to the forward end IS of the electronic endoscope 2, for example, as shown in FIG. 14, and an image of the object 45 is displayed on the monitor 5. Further, a command of manual changeover is sent from the keyboard 7. Setting is made to a state in which only a left-hand image which is image-picked up by the CCD 22L is displayed on the monitor 5. In this connection, the monitor 5 is set to a reference value in the case of a state which previously comes into the reference, for example, in the case where the synchronous signal is finely adjusted so that the display size is variable.

In case where the image of the object 45 is displayed on the monitor 5, the correction coefficient values h1 and v1 which correct the positional shifts (the left- and right-hand shift amounts H1 and the upper and lower shift amounts V1) are inputted from the keyboard 7 in case where the reference position g on the optical axis OL is displayed in shift from the center position Go on the image display area 5a in the monitor 5, like G1, for example. The correction coefficient values h1 and v1 which are inputted from the keyboard 7 are stored in a memory region which corresponds to the positional-shift correction coefficient setting circuit 28 of the EEPROM 28.

The correction-amount operation circuit 29 refers to the correction coefficient values h1 and v1 and outputs the address conversion signal to the H & Y address circuit 30 such that the H & V address which is read out from the 0 (zero) image memory, for example, which stores image-signal data before correction of the frame memory 27 is modified. The H & V address circuit 30 modifies the addresses only through the number of horizontal memory cells and the number of vertical memory cells which correspond respectively to the correction coefficient values h1 and v1, to read out picture elements from the frame memory 27, to thereby correct the positional shift. In the case of FIG. 14, if the H and V addresses which read out a picture element prior to the correction are (A1, B1), the H and V addresses are modified and are read out like (A1+h1/c, B1+v1/c). Here, sign c indicates coefficients which are converted to a scale of the picture elements.

In connection with the above, upon modification of the addresses, in the case where h1/c or the like, for example, does not come into the integer, the modification of the addresses is carried out at an integer portion, while correction which carries out weighting is cazrried out by the adjacent picture element on the side of the interpolation processing circuit 31 with respect to a minority portion. The image-signal data in which the positional shift is corrected are temporarily stored in the first image memory, for example.

Moreover, in the case of being displayed in being inclined as shown in FIG. 14, an inclination-amount correction-coefficient value R1 is inputted from the keyboard 7 in order to correct an inclination angle Θ1 thereof. Then, the inclination-amount correction coefficient value R1 is stored in the memory region which corresponds to the inclination correction-coefficient setting circuit 28b so that a correction value thereof is set. The correction-amount operation circuit 29 outputs the address conversion signal which modifies the address only through an angle −Θ1 which corresponds to the inclination amount correction-coefficient value R1, to the H and V address circuit 30, and outputs the interpolation coefficient to the interpolation processing circuit 31 through the interpolation-coefficient generation circuit 32.

The image-signal data are rotated in which only positional shift is corrected is carried out only through the angle −Θ1 which corresponds to the inclination-amount correction coefficient R1, by the modification of the address and the interpolation processing. The image in which the rotational shift or the inclination is corrected is stored in the second image memory, for example, within the frame memory 27, from the interpolation processing circuit 31. Thus, the state comes into a state in which the image-signal data in which the positional shift and the inclination are corrected are stored in the second image memory.

Further, in the case where the image which is image-picked up by the electronic endoscope 2 is larger than the reference image which is correctly adjusted, or smaller than the same, a magnification correction coefficient value is inputted from the keyboard 7 to carry out magnification correction, in order to make the image have a desired size. Setting of the magnification correction coefficient is carried out by inputting of the magnification correction coefficient value from the keyboard 7.

In the case where the magnification correction is carried out, the vicinity of the center of the image-signal data of the second image memory is enlarged an integer number of times (10 times, for example) to output the image-signal data to the side of the stereo image-signal processing circuit 34. The image-signal data are enlarged and displayed on the monitor 5. The reason why the image in the vicinity of the center is enlarged and is displayed is that the vicinity of the center can be regarded as having almost no distortion.

Figure 15A:
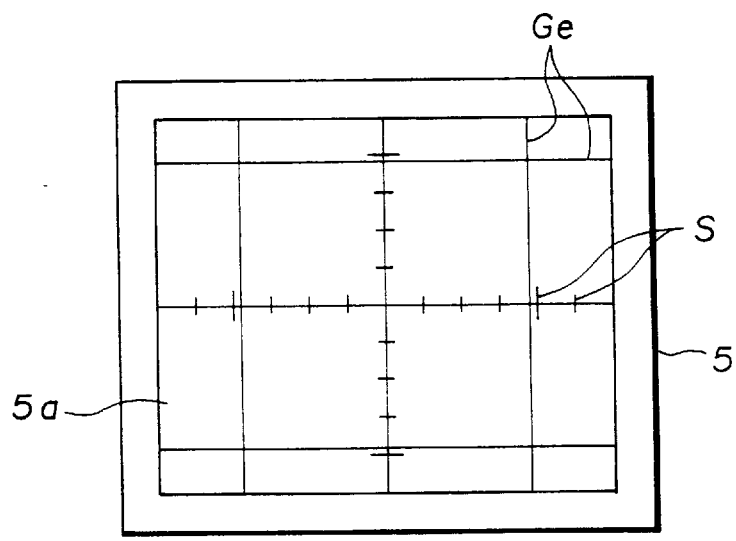
FIG. 15A is an explanatory view in which a center portion is enlarged and is displayed on the monitor.

As shown in FIG. 15A, the length between the lattices of the enlarged image Ge and the reference length between the lattices which is beforehand found from the enlargement of the reference image are compared with each other, and the magnification M of the image Ge (with respect to the image of the reference optical system) due to this optical system is found from the graduation S whose unit is the length between the lattices of the reference image. The magnification correction coefficient value 1/M is inputted from the keyboard 7.

The correction-amount operation circuit 29 refers to the magnification correction coefficient value 1/M, and generates the corresponding address conversion signal and interpolation signal. The correction-amount operation circuit 29 outputs the same to the H and V address circuit 30 and the interpolation processing circuit 31. The correction-amount operation circuit 29 practices processing of the magnification correction with respect to the image-signal data of the second image memory to overwrite the same to, for example, the first image memory. As a result, the image signal data in which the positional shift, the inclination and the magnitude are corrected are stored in the first image memory. That is, the image signal data are image signal data in which only the distortion is not corrected.

Figure 15B:
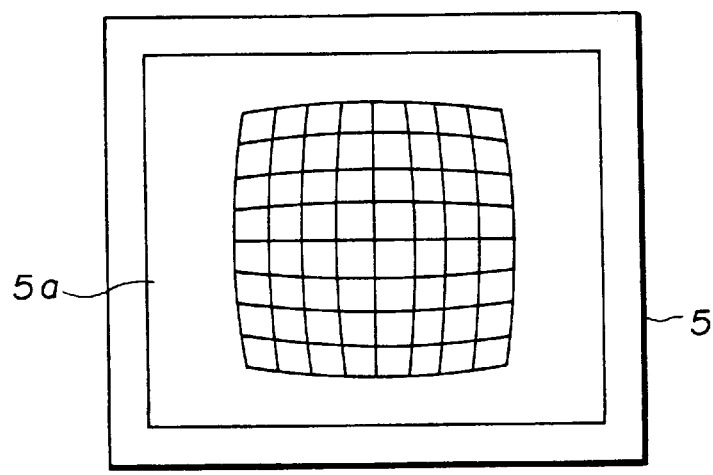

Subsequently, the image signal data of the first image memory are outputted to the side of the stereo image-signal processing circuit 34 and are displayed on the monitor 5 as shown in FIG. 15B.

In the case where the image which is displayed on the monitor 5 is curved or the like as compared with the reference image which is correctly adjusted, the coefficient value which corrects the distortion is inputted from the keyboard 7 to carry out setting of the distortion-value correction-coefficient value. The correction-amount operation circuit 29 carries out an operation to correct the distortion to compute the address conversion signal and the interpolation signal, to output the same to the H and V address circuit 30 and the interpolation processing circuit 31, whereby processing of the distortion correction is carried out with respect to the image signal data of the first image memory. The image signal data in which the processing is carried out are data in which all the four kinds of correction are carried out. The data are outputted to the stereo image-signal processing circuit 34 through the interpolation processing circuit 31.

After the four kinds of image correction have been carried out with respect to the left-hand image in this manner, the forward end 15 of the electronic endoscope 2 is moved only through the distance d in the horizontal direction. Setting is made such that the center g of the object 45 is located at a position which is spaced the predetermined distance T on the optical axis OR of the objective lens system 21R. Further, the command of the manual changeover is sent from the keyboard 7. Setting is made to a state in which only the right-hand image which is image-picked-up by the CCD 22R is displayed on the monitor 5.

Subsequently, operation similar to the above-described operation of the correction is practiced whereby the four kinds of image correction can be practiced with respect to the right-hand image.

If the correction with respect to the left- and right-hand images is completed in this manner, since the information which corrects the positional shift, the inclination (rotation), the size and the distortion of each of the left- and right-hand images is stored in the EEPROM 28 within each of the image correction circuits 25L and 25R, the information which is stored in the EEPROM 28 is subsequently referred to, and operation which corrects the positional shift, the inclination (rotation), the size and the distortion of each of the left- and right-hand images is carried out.

According to the first embodiment, since the image correction is electrically carried out by the image correction circuits 25L and 25R with respect to the respective output signals from the two CCDs 22L and 22R, setting can be made to a state in which the image superior in quality in which the positional shift, the inclination, the size and the distortion of each image is corrected can be displayed.

Since each image which is corrected in this manner is an image in which mutual variation is not just merely corrected, but also a display image in which the positional shift, the inclination or the like of each image per se is dissolved, the operator (or the observer) or the the like can observe the object under the stereo observation state which is superior in quality, which approximates direct observation of the objecct. Thus, if the use is made for a long period of time, fatigue does not occur (the image in which the mutual variation is merely corrected as described above is maintained or remained to an image under an inclined state, for example). That is, it is possible to provide a natural stereo image which is not fatigued even if the observation is made for a long period of time, with respect to the observer.

In other words, in the present embodiment, because the function of the correction means which corrects the mutual variation of the left- and right-hand images, and the factor, for example, like the distortion which is included by the individual images and which deteriorates the image quality are also corrected respectively by the left- and right-hand images, the observer can observe the object under a state which is superior in quality, and which approximates direct observation of the object.

Moreover, according to the present embodiment, since distortion correction is also electrically carried out, it becomes difficult for the lens system which is used in the small objective lens systems 21L and 21R which are disposed within the forward end 15 which is particularly thin in diameter, to avoid the distortion. In the present embodiment, it is possible to provide an image which is superior in quality, which has no distortion or in which the distortion is reduced, even if the lens system having such distortion is used.

Furthermore, since the electrical distortion correction means is provided in this manner, it is possible also to adopt the lens system having the distortion, without the fact that the function of the stereo image display is reduced. Thus, it is also possible to reduce the cost. Further, since the small lens system can be adopted, it is possible to reduce, in diameter, the forward end 15 (which needs not be thickened).

Further, in the present embodiment, even if there are the positional shift, the inclination and the like, they are electrically corrected and can be displayed. Accordingly, since it is possible to widen or enlarge (or relieve) the erroneous range or the like which is permitted in the assembly operation and the adjustment operation for the image-pickup optical system, the adjustment operation or the like can be simplified, and it is possible to reduce the cost also in this aspect.

Moreover, according to the present embodiment, even if the position of the objective lens system, the CCD or the like shifts, or is inclined by secular change or the like, it is possible to easily practice electric correction (it is very difficult to mechanically correct the secular change). Accordingly, it is possible to prevent the display characteristic of the stereo image from being reduced, or to maintain the display function of the stereo image having a high image quality, for a long period of time.

Further, the stereo image processing device 4 in the first embodiment is combined also with the existing electronic endoscope for stereoscopic vision, whereby, if the positional shift and the like exist in the image pickup optical system of the existing electronic endoscope for stereoscopic vision, these are dissolved by the correction so that the function of the image pickup system can be set to the best state. That is, the present embodiment has a wide appliable range (to the contrary, in an arrangement which is mechanically adjusted, an image quality thereof is decided dependent upon the used electronic endoscope for stereoscopic vision).

Figure 16:
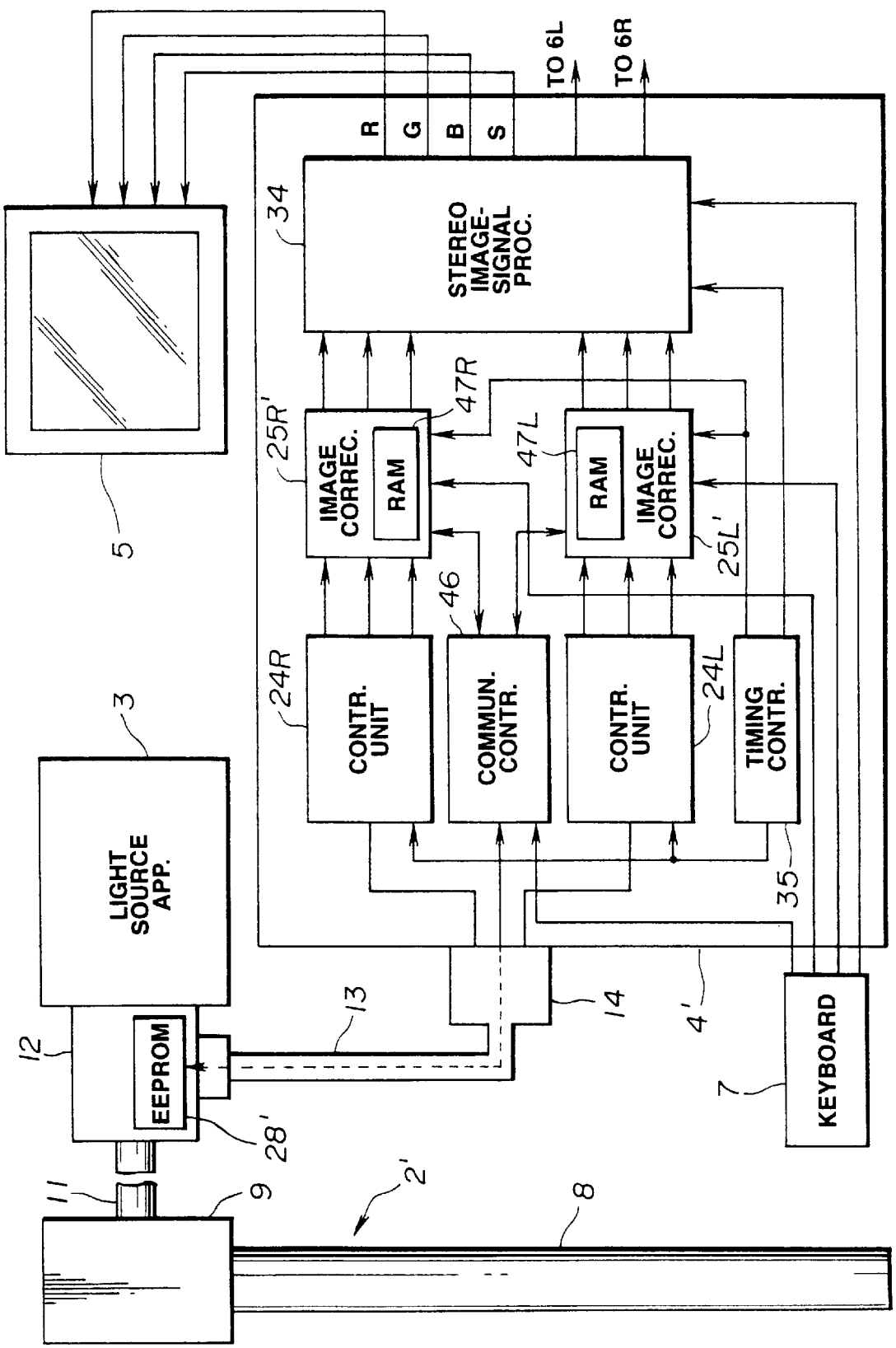
FIG. 16 is an entire arrangement view of a stereoscopic-vision endoscope system according to a second embodiment of the present invention.

FIG. 16 shows a stereo endoscope system 1' according to a second embodiment of the invention. The second embodiment is arranged such that image correction can be practiced which is suited for an image pickup system of an electronic endoscope 2' thereof, in accordance with the electronic endoscope 2' which practically forms the stereo endoscope system 1'. In order to realize the same, the second embodiment is arranged such that memory means for storing information of the image correction is provided within the electronic endoscope 2'.

That is, an EEPROM 28' in which setting information for four kinds of image correction which has been described with reference to the first embodiment is beforehand written is housed, for example, within the light guide connector 12 of the electronic endoscope 2'. The EEPROM 28' is connected to an electrical contact of the signal connector 14 through the signal cable 13.

If the signal connector 14 is connected to a stereo image processing device 4', the EEPROM 28' is electrically connected to a communication controller 46 which is provided within the stereo image processing device 4'. The communication controller 46 is connected to image correction circuits 25L' and 25R' which have RAMs 47L and 47R for storing the information of the image correction, respectively.

Upon activation of the stereo image processing device 4', the communication controller 46 reads out the correction information with respect to the left- and right-hand image pickup systems of the electronic endoscope 2', which is written to the EEPROM 28', and stores the same in the RAMs 47L and 47R.

Moreover, similarly to the first embodiment, the image correction circuits 25L' and 25R' are connected to the keyboard 7, and can also modify information on the RAMs 47L and 47R by command and data inputting from the keyboard 7. The image correction circuits 25L' and 25R' send the command from the keyboard 7 to the communication controller 46, and enables that the information of the EEPROM 28' is reloaded by the information of the RAMs 47L and 47R, through the communication controller 46.

The other arrangement is similar to that of the first embodiment, and the description thereof will be omitted. According to the present embodiment, the image correction value is first set in the RAMs 47L and 47R by operation of the image correction as in the first embodiment, and the set value can be written to the EEPROM 28' of the electronic endoscope 2' through the communication controller 46.

After the information of the correction has been written to the EEPROM 28', the information thereof is automatically transferred to the RAMs 47L and 47R. Accordingly, since the image correction circuits 25L' and 25R' practice processing of the image correction on the basis of the information which is stored in the RAMs 47L and 47R, correction corresponding to the image pickup system of the electronic endoscope 2' which is connected actually is adequately practiced.

That is, in the present embodiment, if the information of the correction is written to the EEPROM 28' of the electronic endoscope 2' by the operation of the image correction, once for the electronic endoscope 2' which is used in the system 1', in case also where any electronic endoscope 2' is subsequently connected, processing of the image correction which is suited for the connected electronic endoscope 2' can automatically be practiced.

In connection with the above, writing operation to the EEPROM 28' by the image correction with respect to the electronic endoscope 2' may be practiced by the side of a maker upon factory delivery or the like.

Furthermore, according to the present embodiment, it is possible to easily update the set value of the image correction in order for the adjustment such as the secular change or the like.

In FIG. 16, the EEPROM 28' is connected to the image correction circuits 25L' and 25R' through the communication controller 46. However, the EEPROM 28' and the image correction circuits 25L' and 25R' may be connected to each other through a cable without the medium of the communication controller 46.

Figure 17:
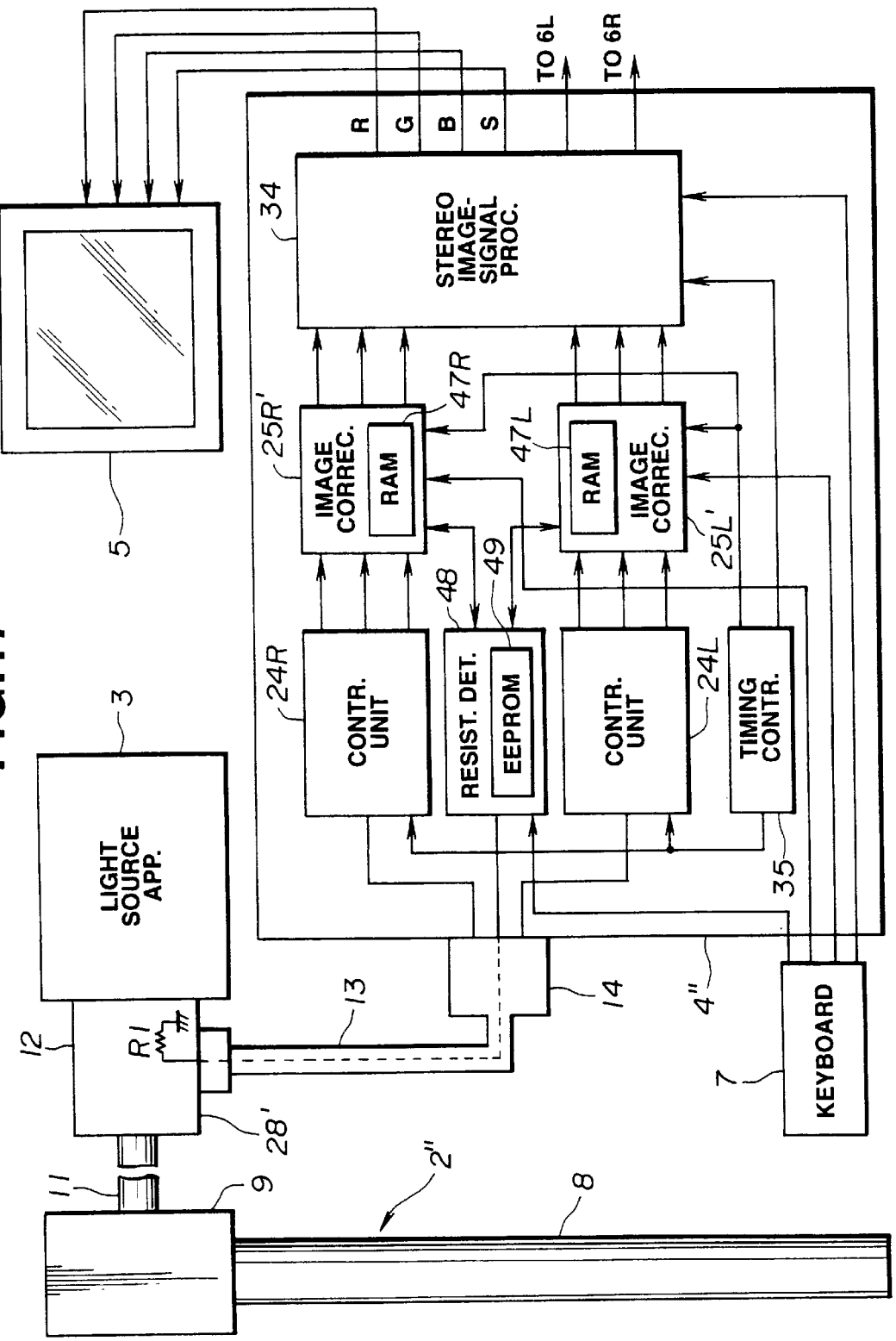
FIG. 17 is an entire arrangement view of a stereoscopic-vision endoscope system according to a third embodiment of the present invention.

FIG. 17 shows a stereo endoscope system 1" according to a third embodiment of the invention. Similarly to the second embodiment, the third embodiment is arranged such that image correction which is suited for an image pickup system of an electronic endoscope 2" can be practiced in accordance with the electronic endoscope 2" which practically forms the stereo endoscope system 1". In order to realize this, in the present embodiment, an identifier (an element to be identified) for identifying the electronic endoscope 2" which is connected to a stereo image processing device 4" is provided on the side of the stereo endoscope 2", and identifying means for identifying the element to be identified is provided on the side of the stereo image processing device 4".

In the materialized or specified example shown in FIG. 17, a resistor R1 which has a resistance value inherent to the electronic endoscope 2", serving as the element to be identified, is housed within, for example, the light guide connector 12 of the electronic endoscope 2". The resistor R1 is connected to an electrical contact of the signal connector 14 through the signal cable 13.

When the signal connector 14 is connected to the stereo image processing device 4", the resistance value of the resistor R1 is electrically connected to a resistance value detection circuit 48 for detecting a resistance value, which is provided within the stereo image processing device 4" so that the resistance value is detected by the resistance-value detection circuit 48. The resistance value is converted to a digital signal of few bits as a detection signal of the resistance value which is detected by the resistance-value detection circuit 48, and is used as an address signal of an EEPROM 49 which stores information of the respective image corrections of the plurality of electronic endoscopes.

Correction information corresponding to the image pickup system of the electronic endoscope 2" which is read out from a storage area corresponding to the assigned address of the EEPROM 49 is transferred to the RAMs 47L and 47R of the respective image correction circuits 25L' and 25R', similarly to the second embodiment.

The image correction circuits 25L' and 25R' refer to the correction information which is transferred to the RAMs 47L and 47R to practice processing of the image correction corresponding to the image pickup system of the electronic endoscope 2" which is practically connected.

Moreover, similarly to the second embodiment, the image correction circuits 25L' and 25R' are connected to the keyboard 7, so that the information of the RAMs 47L and 47R can also be modified by the command and the data inputting from the keyboard 7. The command is sent from the keyboard 7 to the controller within the resistance-value detection circuit 48 to enable also the information of the EEPROM 49 to be reloaded by the information of the RAMs 47L and 47R.

The other arrangement is similar to that of the first embodiment. The third embodiment can practice the image correction which is suited for the image pickup system of the electronic endoscope 2" which is used practically, similarly to the second embodiment.

In connection with the above, the identifying means is not limited to one which practices identification by a resistance value, but may be one which practices identification by bar codes, one which practices identification by existence of pins of the connector, opening and short-circuiting of the pins, or the like.

Figure 18:
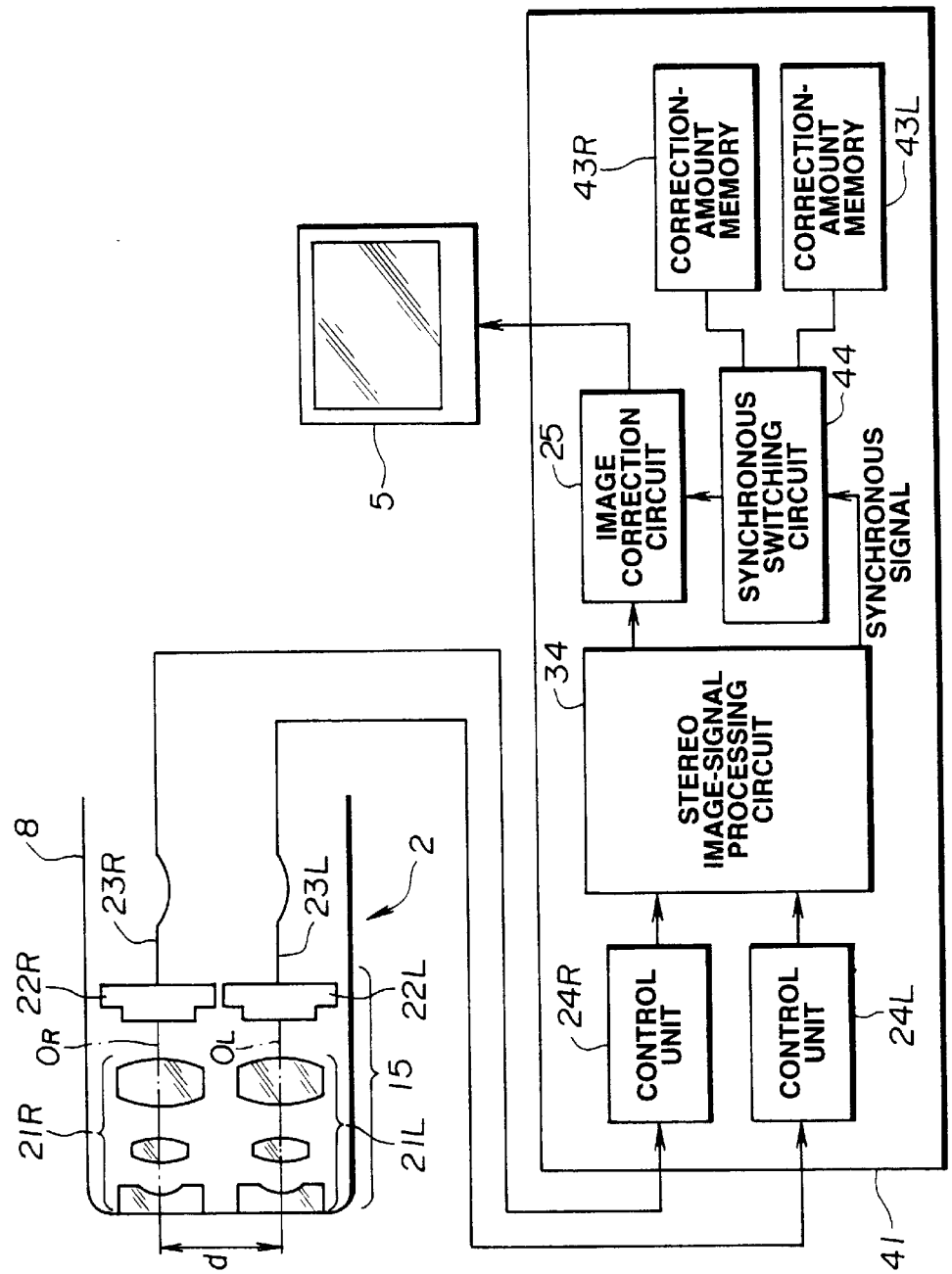
FIG. 18 is a block diagram showing an arrangement of a signal processing system of stereoscopic vision in a fourth embodiment of the present invention.

FIG. 18 shows an image processing circuit 41 in a fourth embodiment of the invention. In the first embodiment, correction of the image is practiced by the two image correction circuits 25L and 25R on the basis of the image signals which are outputted respectively from the control units 24L and 24R. To the contrary, the present embodiment is arranged such that the left- and right-hand images are corrected by a single image correction circuit 25.

Similarly to the first embodiment, the output signals corresponding to the left- and right-hand images which are image-picked-up by the CCDs 22L and 22R which are built in the electronic endoscope 2 are respectively inputted to the control units 24L and 24R, and are converted to left- and right-hand image signals. In the present embodiment, the left- and right-hand image signals are inputted to the stereo image-signal processing circuit 34.

Provided are correction-amount memories 43L and 43R which store the respective correction amounts such that the left-hand image correction amount acts upon a left-hand image signal in the left-hand image, while the right-hand image correction amount acts upon a right-hand image signal in the right-hand image, in synchronism with the read-out period, with respect to the left- and right-hand image signals which are outputted in time sharing from the frame memory within the stereo image-signal processing circuit 34, a synchronous switching circuit 44 for switching the correction amount memories 43L and 43R in synchronism with the left- and right-hand image signals which are outputted from the stereo image-signal processing circuit 34, to output the same to the image correction circuit 25, and the image correction circuit 25 for practicing correction by the switched correction amount.

Figure 1A:
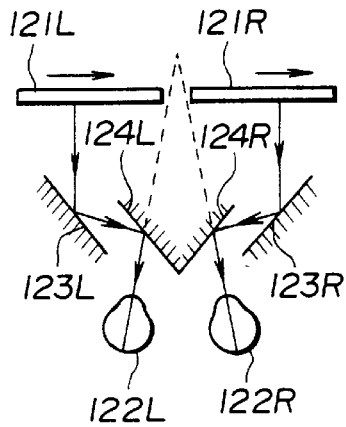
FIGS. 1A to 1C are explanatory views of the prior art showing a method of displaying an image which is stereoscopically viewed.
Figure 1B:
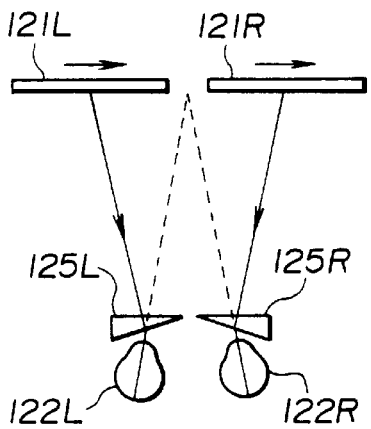
Figure 1C:
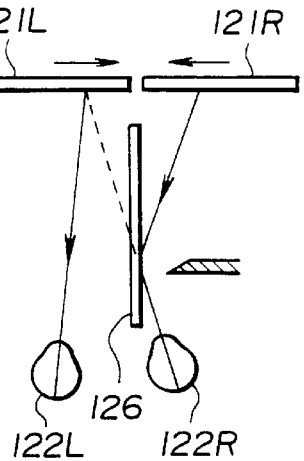
Figure 2:
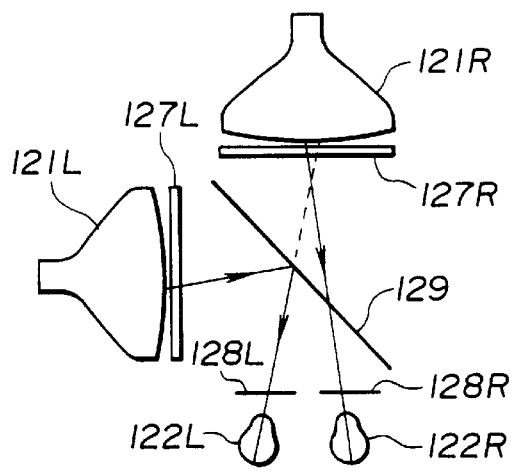
FIG. 2 is an explanatory view showing another prior art method of displaying an image which is stereoscopically viewed.
Figure 3:
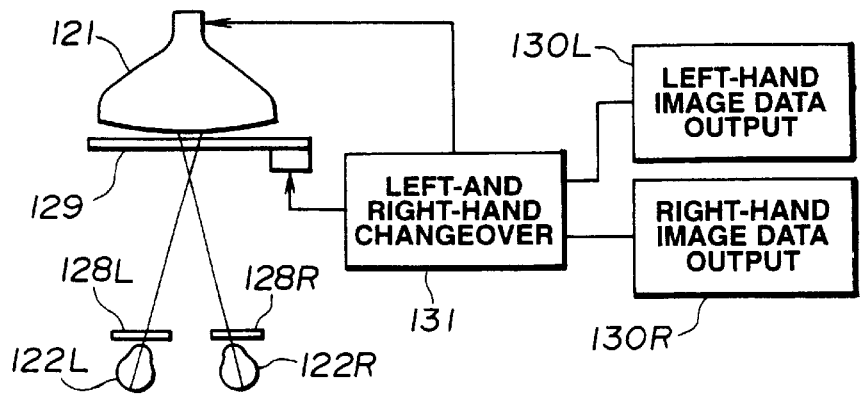
FIG. 3 is an explanatory view showing another prior art method of displaying an image which is stereoscopically viewed.
Figure 4:
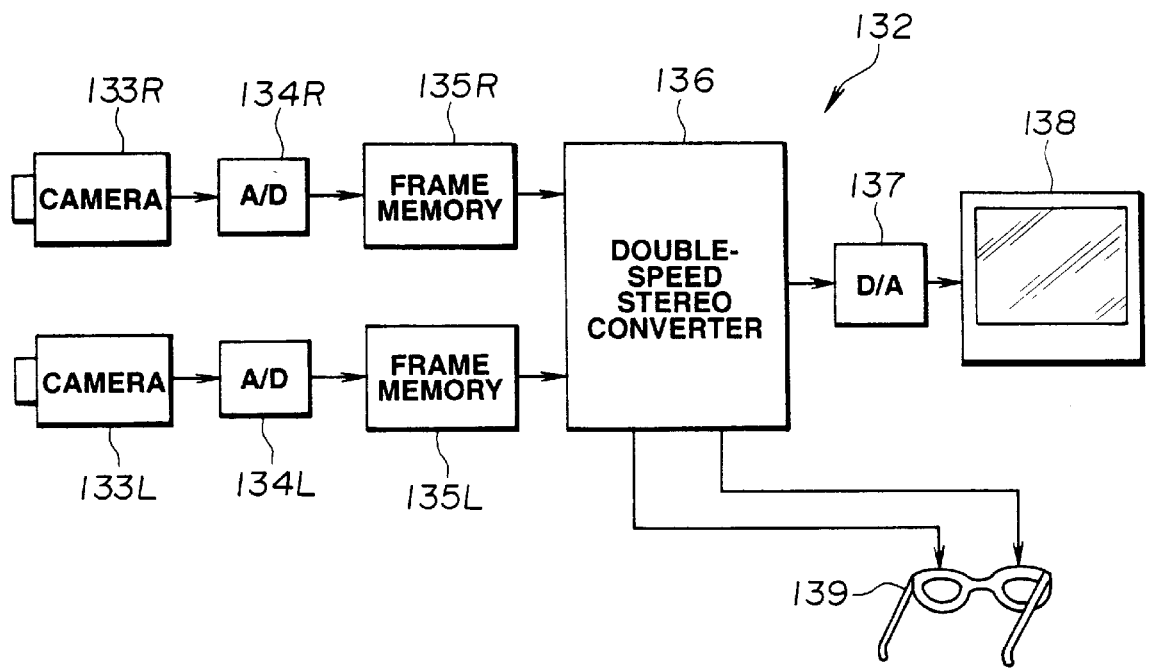
FIG. 4 is a block diagram view showing a prior art signal processing system of stereoscopic vision.
Figure 5:
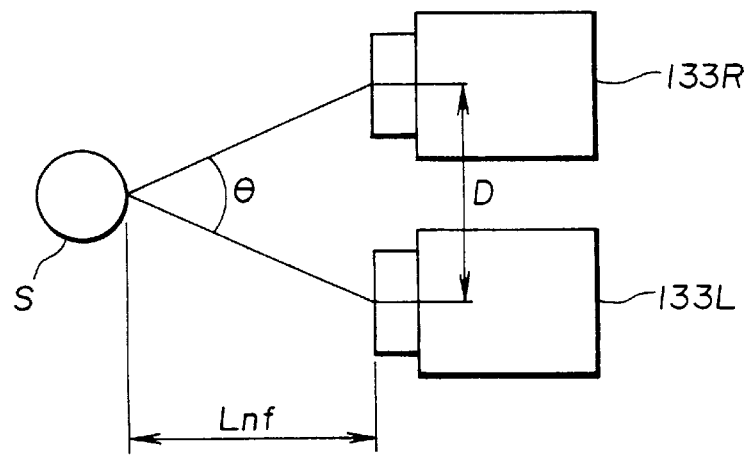
FIG. 5 is an explanatory view of an inward angle when an image is stereoscopically picked-up.

Correction-amount data which correct, respectively, a magnification, a rotational amount, a distortion amount and a shift amount are stored in the correction-amount memories 43L and 43R. The correction amount memories 43L and 43R are arranged, respectively, by EEPROMs, for example, similarly to the first embodiment, for example, and can electrically reload the correction-amount data. The correction-amount data of the correction-amount memories 43L and 43R are set through a CPU or the like (not shown) from the keyboard 7 or the like. The other arrangement is similar to that of the first embodiment. In this connection, in FIG. 18, the timing controller 35 and the spectacles 6 for stereoscopic vision in FIG. 2 are omitted.

In the fourth embodiment, the image correction circuit 25 is disposed in a rear stage of the stereo image-signal processing circuit 34, whereby the left- and right-hand image signals can be corrected independently by the single image correction circuit 25. Specifically, the fourth embodiment is arranged so as to practice function substantially similar to that of the first embodiment, by the single image correction circuit 25. Accordingly, the fourth embodiment has advantages similar to those of the first embodiment and, further, has advantages of simplification of the arrangement of the system and reduction of the cost price more than those of the first embodiment.

Figure 19:
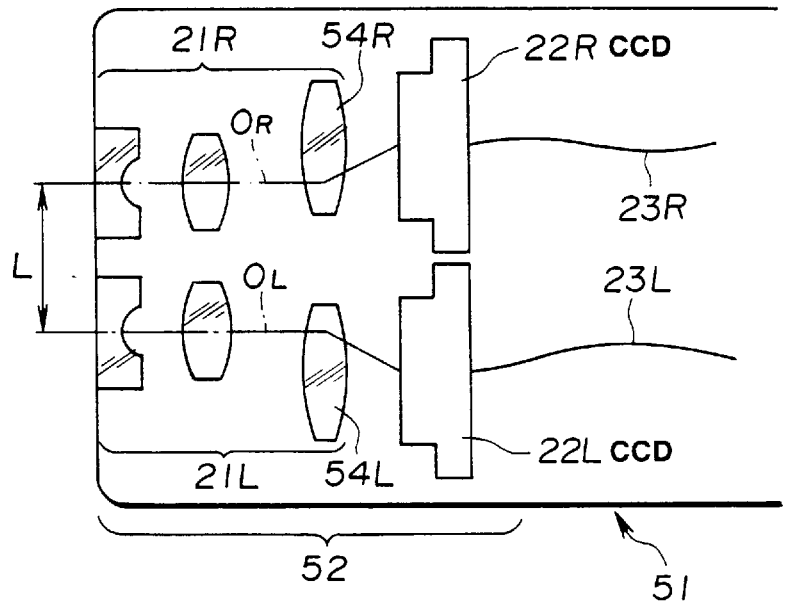
FIGS. 19 and 20 relate to a fifth embodiment of the present invention, FIG. 19 showing a summary arrangement of an image pickup optical system at a forward end of an insertion part in the fifth embodiment.

FIG. 19 shows a forward end 52 of an electronic endoscope 51 in a fifth embodiment of the invention. The electronic endoscope 51 in the fifth embodiment is a stereoscopic-vision electronic endoscope of type which is suitable to one for proximity observation.

As shown in FIG. 19, objective lens systems 53L and 53R in the forward end 52 are disposed such that an interval L between front group systems of the respective adjective lens systems 21L and 21R is such that an inward angle is equal to or less than 20°, upon proximity or nearby observation. The arrangement is such that lenses 54L and 54R of rear group systems of the objective lens systems 53L and 53R (or on the side of the CCDs 22L and 22R) are eccentrically disposed such that the respective optical axes OL and OR are so bent outwardly as to become symmetric with respect to a longitudinal direction of the insertion part (left- and right-hand directions in FIG. 19) in accordance with the magnitudes of the adjacent CCDs 22L and 22R.

The optical axis on the side of the front group system, that is, the optical axis which becomes parallel to the longitudinal direction of the insertion part becomes such an optical axis as to be bent to spread outwardly to the left- and right-hand sides from a position where the lenses 54L and 54R are disposed, by the lenses 54L and 54R which are eccentrically disposed left-outwardly and right-outwardly, respectively, so as to be directed toward the centers of the CCDs 22L and 22R.

Figure 20:
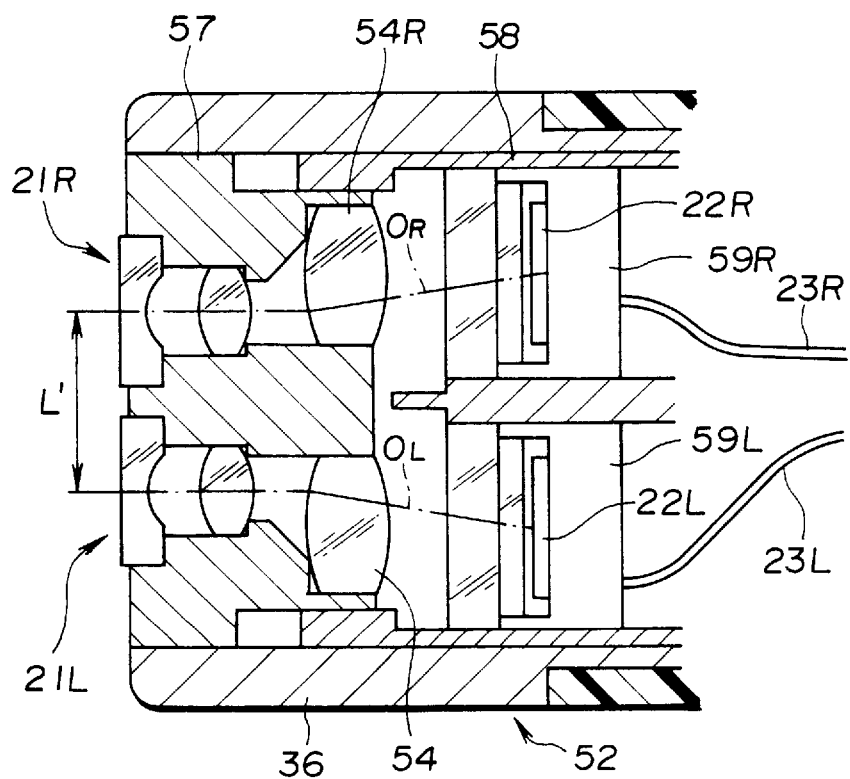

FIG. 20 shows a structure of the forward end 52 in which FIG. 19 is shown more concretely or specifically. An objective lens unit 57 is fitted in a through-bore which is provided in the forward-end member 36, and two objective lens systems 21L and 21R are integrally mounted on the objective lens unit 57. Moreover, a CCD unit 58 having a front-end side which is fitted in a rear-end side of the objective lens unit 57 is fitted in the through-bore. The CCDs 22L and 22R are integrally mounted on the CCD unit 58.

The arrangement is such that an interval between the objective lens unit 57 and the CCD unit 58 is adjusted or regulated whereby focus adjustment can be practiced once with respect to both the image pickup optical systems (both the objective lens systems 21L and 21R and both the CCDs 22L and 22R). After the focus adjustment, the objective lens unit 57 and the CCD unit 58 are fixed to the forward end member 36 by fixing screws or an adhesive (not shown).

As described above, the lenses 54L and 54R are fixed to the objective lens unit 57 such as to be eccentrically disposed outwardly to the left and outwardly to the right more than the optical axis of the front group system.

The other arrangement is similar to that of the first embodiment or the fourth embodiment.

The optical axes OL and OR of the respective objective lens systems 21L and 21R are angled outwardly so as to become symmetric with respect to both the left- and right-hand sides in the direction of the center axis of the insertion part by the lenses 54L and 54R, respectively, whereby the interval L between the objective lens systems 21L and 21R can be set such that a desired parallax is acquired, without receipt of interference of packages 59L and 59R of the respective CCDs 22L and 22R.

Furthermore, there is a great advantage in that distortion of the image which is generated from decentering of the optical system can be removed by the image correction circuit correspondingly to the respective images, it is possible to acquire a natural and desired feeling of three-dimension, and it is possible to reduce the diameter of the forward end 52. The other advantages are substantially similar to those of the first embodiment or the second embodiment.

Figure 21:
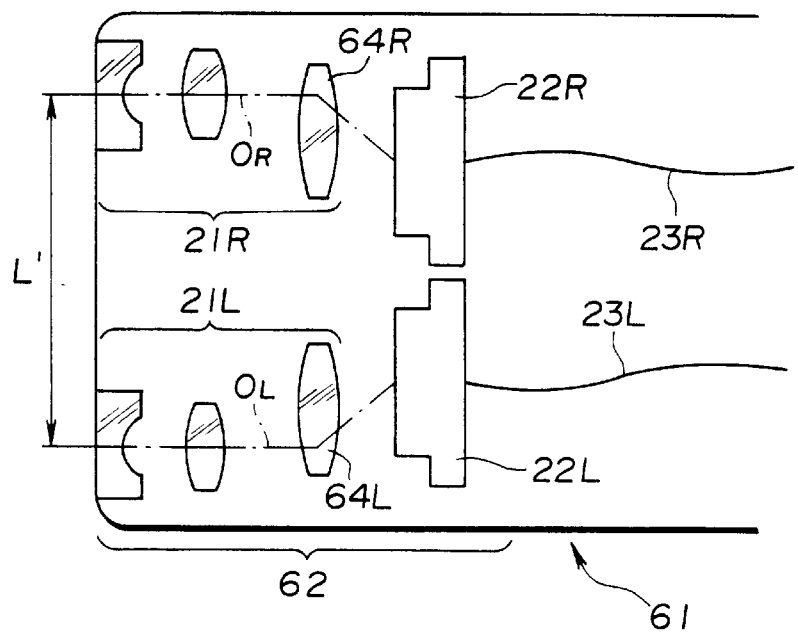
FIGS. 21 and 22 relate to a sixth embodiment of the present invention, FIG. 21 showing a summary arrangement of an image pickup optical system at a forward end of an insertion part in the sixth embodiment.

FIG. 21 shows a forward end 62 of an electronic endoscope 61 in a sixth embodiment of the invention. The electronic endoscope 61 in the sixth embodiment is an electronic endoscope for stereoscopic vision of type which is suitable for great distance observation.

As shown in FIG. 21, the forward group system of the objective lens systems 21L and 21R are disposed to an interval L' such that the inward angle becomes equal to or more than 2° also when the objective lens systems 21L and 21R in the endoscope forward end 62 observe considerably a great distance. Lenses 64L and 64R which are the closest to the CCDs 22L and 22R in the objective lens systems 21L and 21R are eccentrically disposed such that the optical axes OL and OR are bent inwardly so as to become symmetric with respect to the longitudinal direction of the insertion part, in conformance with the magnitude of the adjacent CCDs 22L and 22R.

The lenses 64L and 64R are eccentrically disposed inwardly to the right and inwardly to the left more than the optical axis of the front group system, whereby, as shown in FIG. 21, the optical axes OL and OR are bent so as to become narrow inwardly to the right and the left from positions where the lenses 64L and 64R are disposed, resulting in such optical axes as to reach center positions of the CCDs 22L and 22R.

Figure 22:
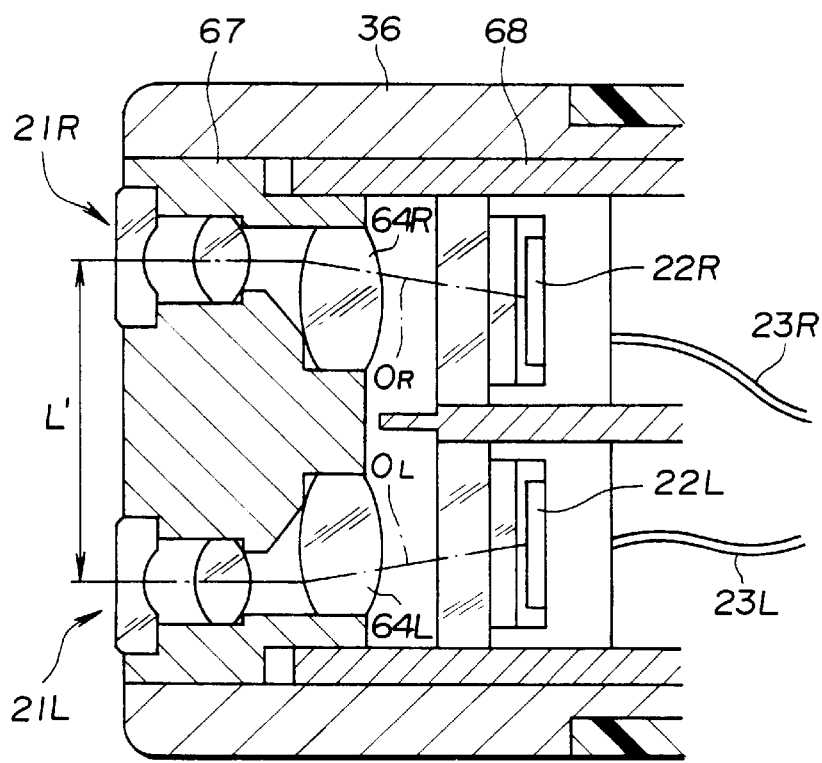

FIG. 22 shows a structure of the forward end 62 in which FIG. 21 is shown more specifically. An objective lens unit 67 is fitted in the transparent bore or the through-bore which is provided in the forward-end member 36. The two objective lens systems 21L and 21R are integrally mounted on the objective lens unit 67. Moreover, a CCD unit 68 having a forward-end side which is fitted in a rearward-end side of the objective lens unit 67 is fitted in the through-bore. The CCDs 22L and 22R are integrally mounted on the CCD unit 68. An interval between the objective lens unit 67 and the CCD unit 68 is adjusted whereby the focus adjustment can be practiced once. After the focus adjustment, the objective lens unit 67 and the CCD unit 68 are fixed to the forward-end member 36 by fixing screws or an adhesive (not shown).

As described above, lenses 64L and 64R are fixed to the objective lens unit 67 so as to be eccentrically disposed inwardly to the left and inwardly to the right more than the optical axis of the front group system.

The other arrangements are similar to that of the first embodiment or the fourth embodiment.

Chiefly, in an industrial endoscope, there are cases which cannot approach the observation object, and there are also cases where a distance from the forward end of the endoscope to the object increases. In the present embodiment, in order that the stereoscope-vision observation can be practiced also upon observation of a great distance, the interval between the objective lenses 21L and 21R increases as far as possible, and the optical axes OL and OR are bent inwardly on the side of the image pickup element, whereby the interval between the CCDs 22L and 22R can be reduced, and the outer diameter of the forward end 62 can be reduced. Further, similarly to the fifth embodiment, distortion of the image of the optical system due to eccentricity or decentering is corrected by the image correction circuit.

Figure 23:
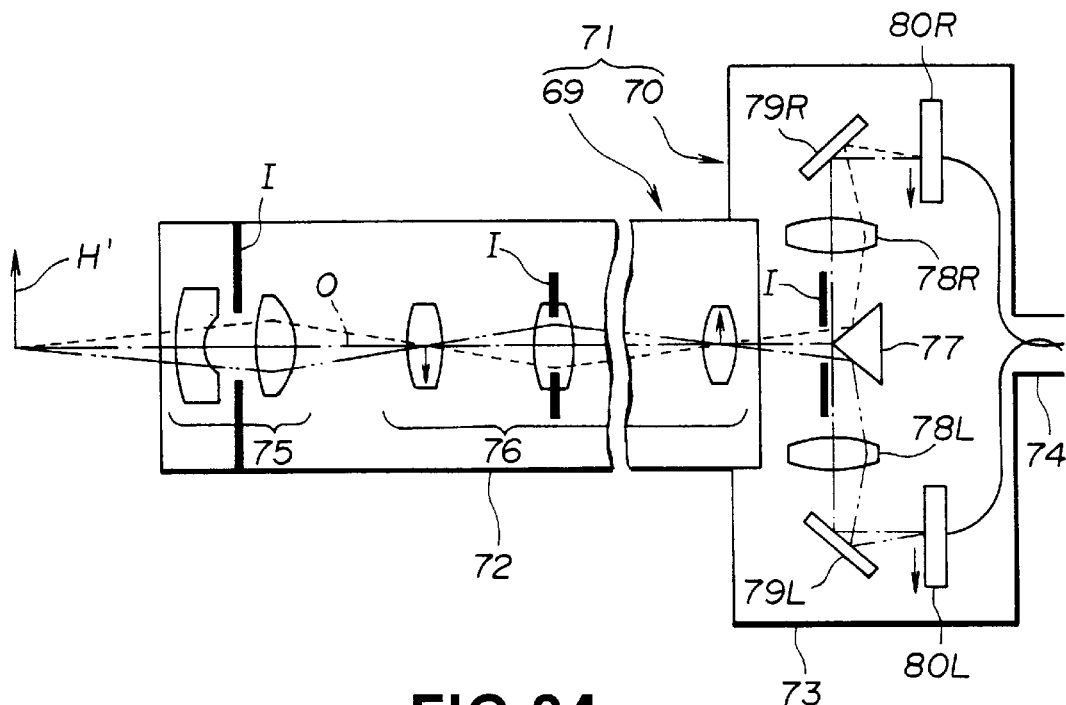
FIG. 23 is a view showing a summary arrangement of an image pickup optical system of an electronic endoscope for stereoscopic vision in a seventh embodiment of the invention.

FIG. 23 shows an electronic endoscope 71 for stereoscopic vision in a seventh embodiment of the invention. The electronic endoscope 71 for stereoscopic vision uses a pupil-division type optical system in the image pickup optical system, and is chiefly useful in a mirror system of a hard electronic endoscope sufferinng from a limit in the outer diameter of the insertion part.

The electronic endoscope 71 for stereoscopic vision is formed with a hard and elongated insertion part 72 and a grasped part 73 which is wide in width and which is formed at a rear end of the insertion part 72. A cable 74 extends from the grasped part 73, and is connected to the stereo image processing device 4 or the like of the first embodiment.

A single set of objective lens system 75 which is used in common in left and right are disposed at a forward end of the insertion part 72 to image-form an image of an object H' which is indicated by an arrow, in front of the objective lens system 75. The image-formed image is transmitted to the rear of the grasped part 73 by a relay lens system 76 which serves as an image transmission optical system (more particularly, a relay optical system which focuses into an image so as to relay the same, to transmit the image toward the rearward side) which is disposed within the insertion part 72 along an optical axis O of the objective lens system 75 so as to be coincident with the optical axis O.

A pupil division prism 77 serving as pupil division means is disposed at a pupil position (or the vicinity thereof) in opposed relation to the final relay lens of the set of relay lens system 76 such that an apex thereof is positioned on the optical axis O to divide the pupil. By the pupil division prism 77, the transmitted image is divided into left- and right-hand images. Light rays which are divided by the pupil division prism 77 pass respectively through imaging lenses 78L and 78R and mirrors 79L and 79R which correspond respectively thereto, and are imaged onto CCDs 80L and 80R. In this connection, in FIG. 23, a black thickened line indicates a stop I. Further, a light guide is omitted.

In connection with the above, a detachable structure may be employed between the relay lens system 76 and the pupil division prism 77, for example, in the image pickup optical system (in FIG. 23, the reference numerals 75–79R) which is adapted to focus into an image of the object H' to the CCDs 80L and 80R, for example, between a distal end of the insertion part 72 and the grasped part 73, or on the way of the grasped part 73. In FIG. 23, the side of a body 69 having the insertion part 72 and the side of an image pickup part 70 having the CCDs 80L and 80R are made to a detachable or separable structure at a location between the relay lens system 76 and the pupil division prism 77.

Advantages of a case where such structure is employed are as follows: That is, the side of the body 69 having the insertion part 72 which is contaminated within the body and the side of the image pickup part 70 having built therein the CCDs 80L and 80R which serve as an image pickup element, and which are not inserted into the body can be separated from each other. In addition, only the side of the body 69 which has the insertion part 72 may be sterilized or disinfected, which, basically, time is consumed after using.

Specifically, advantages of a case where such structure is employed can be mentioned as follows: That is, in a structure which is not detachable, the expensive image pickup part having built therein the image pickup element, or an expensive camera head part is also so required to be dealt with together for sterilization or disinfection of the side of the insertion part. Accordingly, many image pickup parts or camera head parts must be prepared. To the contrary, in a structure which is detachable, several sides of the body 69 having the insertion part 72 are prepared. The number of the expensive image pickup parts or camera head parts need be reduced (since sterilization or disinfection thereof is not almost necessary, they can almost always be reused).

Moreover, in a hard endoscope, a strabismus optical system such as 30°, 70° or the like becomes necessary in accordance with the observation part, other than a direct vision system. Such great advantages can also be acquired that, at this time, it is dispensed with easily by replacement of only the side of the insertion part and, further, it is possible to prepare the system at a low cost.

In this manner, in case where the side of the body 69 and the side of the image pickup part 70 or the camera head can be replaced from each other and are detachable, it is desired to practice image correction in accordance with a combination thereof. For example, this may be carried out as an eighth embodiment (to be described subsequently).

Figure 24:
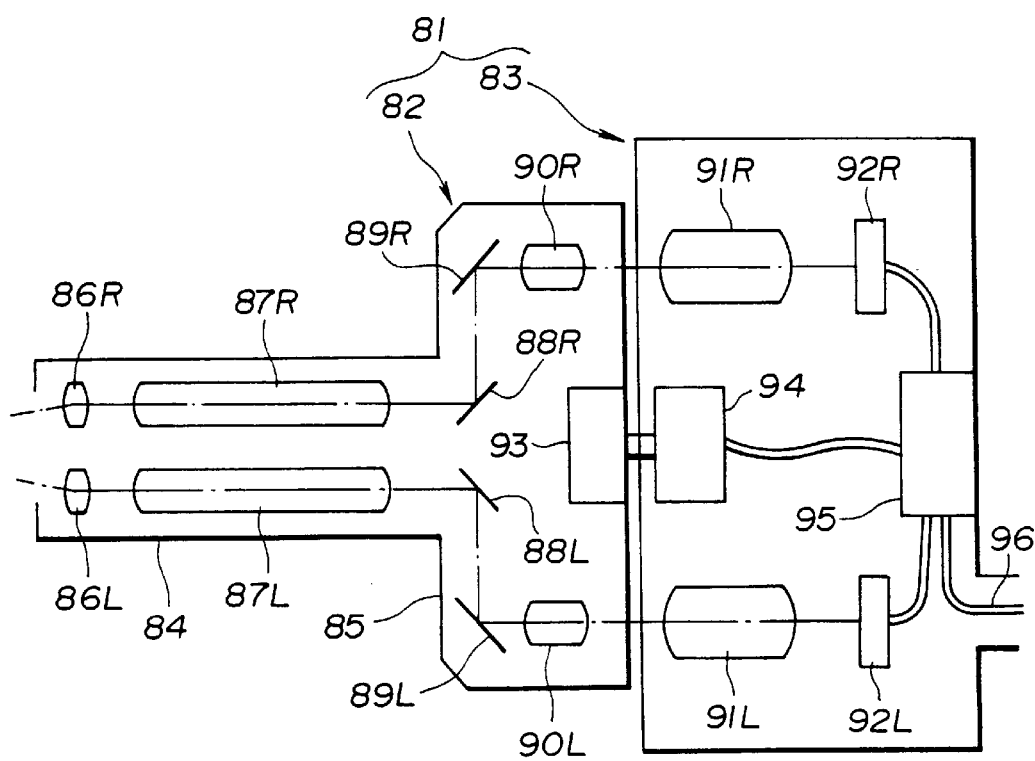
FIG. 24 is a view showing a summary arrangement of an image pickup optical system of a rigid endoscope in an eighth embodiment of the present invention.

FIG. 24 shows a hard endoscope 81 in the eighth embodiment of the invention. The hard endoscope 81 comprises a hard endoscope body (referred also to as "scope body") 82, and a camera head part 83 which is detachable from the scope body 82.

The scope body 82 has a hard insertion part 84 and a grasped part 85, and has a structure in which a camera head part 83 having built therein an image pickup element can be mounted on a distal end of the grasp part 84. A pair of left- and right-hand objective lenses 86L and 86R are disposed at a forward end of the insertion part 84. Left- and right-hand images which are image-formed by these objective lenses 86L and 86R are transmitted to the side of the grasp part 85 by relay lens parts 87L and 87R, respectively.

The images which are transmitted to the side of the grasped part 85 are reflected, respectively, by the pairs of mirrors 88L and 89L and 88R and 89R and advance along optical axes which are spaced to the left and right from each other. The images pass through lenses 90L and 90R and image-forming lenses 91L and 91R within the camera head part 83, and are image-formed on CCDs 92L and 92R, respectively.

The present embodiment is arranged by the use of so-called two relay optical systems which have the scope body 82 in which objective lenses 86L and 86R and relay lens parts 87L and 87R are arranged to the left and right in parallel to each other, and the camera head part 83 which is separable from the scope body 82 and in which the image-forming lenses 91 L and 91R and the CCDs 92L and 92R corresponding respectively thereto are disposed.

An image correction memory 93 for correcting variation or the like of images which are generated respectively by the objective lenses 86L and 86R and the relay lens parts 87L and 87R is provided in the vicinity of, for example, the distal end of the grasp part 85 within the scope body 82. Furthermore, a readout device 94 for reading out a signal from the image correction memory 93 on the side of the scope body 82 and an image correction memory 95 for correcting variation of the camera head part 83 are provided on the side of the camera head 83. The arrangement is such that information which is acquired thereat is sent to the stereo image processing device 4' shown, for example, in FIG. 16, through a transmission line 96.

The image correction memories 93 and 95 are provided respectively on the scope body 82 and the camera head part 83, respectively, whereby such advantages can be acquired that it is possible to cope with many kinds of combinations of the scope body and the camera head body.

Specifically, use can be made also by a combination between a scope body which is different from the scope body 82 shown in FIG. 24 and the camera head part 83 shown in FIG. 24. Reversely, use can also be made by a combination of the scope body 82 shown in FIG. 24 and a camera head part which is different from the camera head part 83 shown in FIG. 24.

Even if the combination is changed in this manner, the correction information for correcting the respective variations, distortions or the like is provided on each of the scope bodies and each of the camera heads, and the arrangement is such that, in the case where these are used in combination, the correction information is read out and is corrected on the side of the stereo image processing device. Accordingly, when used in combination, even if setting of the correction amount is not practiced one by one, it is possible to display the stereo image in which variation or the like is corrected, onto the display means. There are also other advantages similar to those of the first embodiment or the like.

Figure 25A:
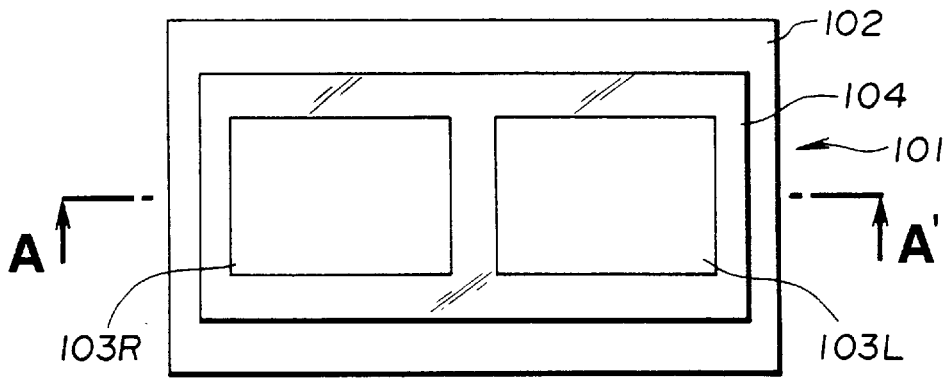
FIGS. 25A and 25B relate to a ninth embodiment of the present invention, FIG. 25A being a top plan view showing an arrangement of an image pickup element for stereoscopic vision in the ninth embodiment.
Figure 25B:
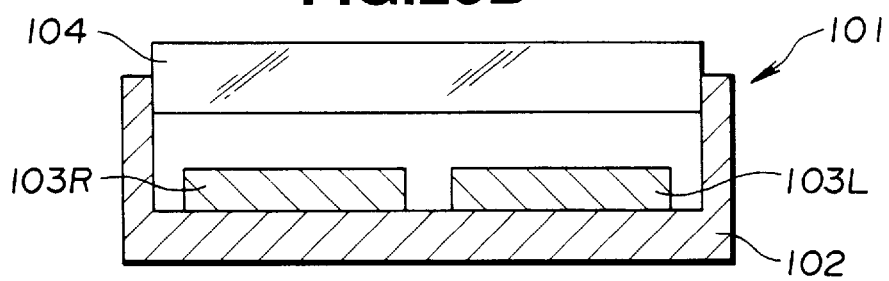

FIGS. 25A and 25B show an image pickup element 101 for stereoscopic vision in a ninth embodiment of the invention. FIG. 25A shows the image pickup element 101 for stereoscopic vision by a top plan view, while FIG. 25B shows an A–A' cross-section in FIG. 25A.

The image pickup element 103 for stereoscopic vision is of a structure in which image pickup element chips 103L and 103R for a left-hand image and a right-hand image are disposed in a row in a recess in a package 102 in parallel to left- and right-hand directions (a horizontal direction in FIG. 25A) such that photoelectric conversion surfaces come into upper surfaces. The arrangement is such that a transparent plate 104 provided with function of cover glass material (function to protect the interior and to transparentize light) is arranged on upper surfaces of both the image pickup element chips 103L and 103R and is adhered to an upper end thereof to which the package 102 opens, to close both the image pickup element chips 103L and 103R which are disposed within the package 102.

The two image pickup element chips 103L and 103R for picking-up in image the left-hand image and for picking up in image the right-hand image are provided on the single package 102, whereby it is possible to reduce the magnitude (size) as an image pickup element for stereoscopic vision less than case where image pickup element chips are provided respectively on the packages. A pair of objective lens systems are provided on the side of the upper surface in FIG. 25A, whereby it is possible to form an image pickup device for electronic vision.

Moreover, there are provided the following advantages. That is, in addition to normal glass material, a filter having low-pass function for preventing interference fringe from being generated by light receiving elements (referred to as "picture element") which are arranged two-dimensionally, and which respectively form the image pickup element chips 103L and 103R, such as material having birefringence function, a diffraction grating or the like and a periodic structure of an object, color-temperature correction glass material for practicing correction of the color temperature, or a low-pass filter to which infrared-ray cut coating for cutting an infrared ray, or the like is applied is substituted for the transparent plate 104, whereby two transparent plates, in sum, are normally necessary for each of the objective lens systems. However, a single transparent plate is sufficient.

Furthermore, a frame structure in the vicinity of the image pickup element is made simple by the fact that the left- and right-hand CCDs are integrated with each other. There are also provided great advantages that, in case where storage is made in the forward end of the endoscope, an outer diameter thereof can be reduced.

Figure 26A:
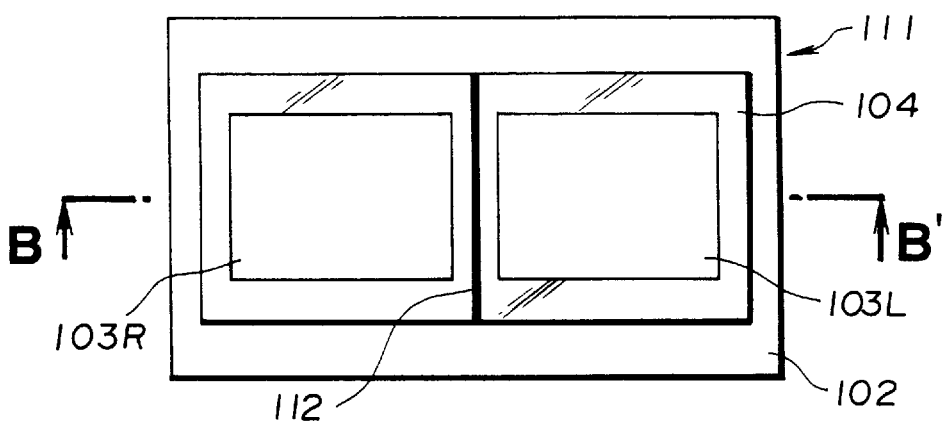
FIGS. 26A and 26B relate to a tenth embodiment of the present invention, FIG. 26A being a top plan view showing an arrangement of an image pickup element for stereoscopic vision in the tenth embodiment.
Figure 26B:
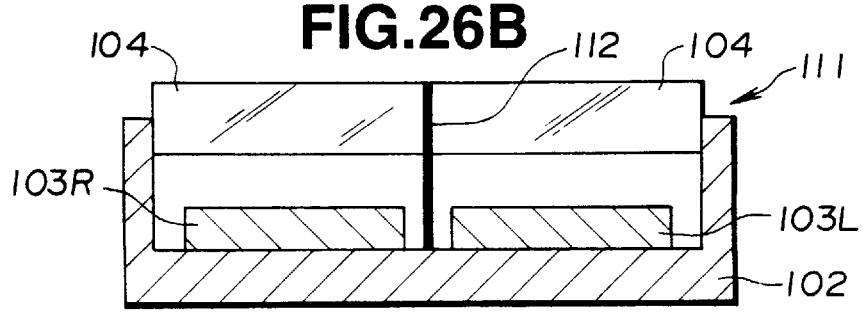

FIGS. 26A and 26B show an image pickup element 111 for stereoscopic vision in a tenth embodiment of the invention. Similarly to case of FIGS. 25A and 25B, FIG. 26A shows the image pickup element 111 for stereoscopic vision by a top plan view, while FIG. 26B shows a cross-sectional view in FIG. 26A. The image pickup element 111 for stereoscopic vision is one which improves the ninth embodiment, and is arranged such that a light shielding plate 112 made of a thin metallic plate is provided between the image pickup element chips 103L and 103R shown in FIGS. 25A and 25B, and stray lights adjacent to each other are shielded in light.

The light shielding plate 112 has both surfaces thereof which are painted with black or with another light absorbent color. Thus, reflection by the light shielding plate 112 is also prevented. The light shielding plate 112 is not particularly limited to a metallic plate, but may use insulating material such as ceramics or the like, and an arrangement in which a light shielding part is integrally formed on a package per se. The other arrangements are similar to those of the ninth embodiment.

In the present embodiment, the light shielding plate 112 is provided between the image pickup element chips 103L and 103R, whereby such a phenomena (due to stray light) that light incident upon toward one image pickup element chip (103L, for example) is incident upon the other image pickup element chip (103R, for example) by the transparent plate 104 due to multipath reflection or the like is secured to be prevented by the light shielding plate 112.

The present embodiment has advantages similar to those of the ninth embodiment, and has an advantage that the phenomena due to the stray light is prevented.

In connection with the above, the first embodiment, for example, is so arranged as to correct the magnitude, the distortion, the inclination and the positional shift of the image. However, the present invention should not be limited to this arrangement, and includes an arrangement which electrically corrects one or more thereof independently with respect to the left and right. For example, the objective lens systems 21L and 21R or the like are formed by lens systems having distortion. However, in the case where an assembling operation can be practiced with high precision, there may be a case where it is sufficient only if correction of the distortion is practiced. The present invention includes also such case.

In connection with the above, embodiments or the like which are arranged such that the above-described embodiments or the like are partially combined with each other, or the like, belong to the present invention.

As described above, according to the present invention, in the stereoscopic-vision endoscope system comprising the endoscope for stereoscopic vision having the image pickup means for stereoscopic vision for leading two object images having the parallax, to the two image pickup elements through the objective optical system which is disposed at the forward end of the elongated insertion part, the image-signal conversion means for converting the two image pickup signals photoelectrically converted by the two image pickup elements to the stereo image signals for practicing stereoscopic vision, and the display means for displaying the stereo image signals, the image correction circuit for electrically optionally correcting independently at least one of the magnitude, the distortion, the inclination and the positional shift of the image, with respect to two image pickup signals which are acquired through the objective optical system and the image pickup element is provided whereby, even under a state where the objective optical systems which are disposed at the forward end have distortion or the like, the image can be corrected to such an image as to describe the object more faithfully, and variation of the left- and right-hand images, or the like, can also be dissolved. Accordingly, it is possible to display the image for stereoscopic vision which is superior in quality, and which is suited for practicing stereo observation. Thus, it is possible to provide, to the observer, a stereo image which is natural and which produces less fatigue even if observation is practiced for a long period of time.

What is claimed is:

1. A stereoscopic-vision endoscope system comprising:

an endoscope for stereoscopic vision having a distal part including an elongated insertion part, a proximal part to be grasped, an output means for outputting illumination light for illuminating an object from an illumination window which is provided in a forward end of said insertion part, an objective optical system provided in the forward end of said insertion part for focusing two images having a parallax with respect to said object which is illuminated by said illumination light, and two image pickup elements for photoelectrically converting said two images at least on the basis of said objective optical system;

image-signal conversion means for converting two image signals photoelectrically converted by said two image pickup elements to a stereo image signal for stereoscopic viewing;

display means for displaying said stereo image signal so as to be recognizable by an observer as a stereoscopic image, and image correction means for electrically correcting at least one of magnitude, aberration distortion, inclination and a positional shift of said two image signals, independently of each other in real time.

2. A stereoscopic-vision endoscope system according to claim 1, wherein said endoscope for stereoscopic vision is an electronic endoscope in which said two image pickup elements are disposed respectively at positions where said objective optical system focuses said two images.

3. A stereoscopic-vision endoscope system according to claim 2, wherein said objective optical system includes two objective lens systems which are disposed in parallel to each other in left-hand and right-hand directions perpendicular to an axial direction of said insertion part, and wherein said two objective lens systems have two first objective lenses which are disposed respectively on left-hand and right-hand optical axes which are in parallel to the axial direction of said insertion part, and two second objective lenses disposed closer to said two image pickup elements than are said two first objective lenses, for converting said left-hand and right-hand optical axes to optical axes which are angled respectively in left-hand and right-hand outward directions.

4. A stereoscopic-vision endoscope system according to claim 3, wherein said two second objective lenses are eccentrically disposed from said left-hand and right-hand optical axes, and wherein said two image pickup elements are disposed at positions for detecting said two images respectively formed by said two second objective lenses.

5. (Amended) A stereoscopic-vision endoscope system according to claim 2, wherein said objective optical system has two objective lens systems which are disposed in parallel to each other in left-hand and right-hand directions perpendicular to an axial direction of said insertion part, wherein said two objective lens systems have two first objective lenses disposed respectively on left-hand and right-hand optical axes which are in parallel to the axial direction of said insertion part, and two second objective lenses disposed closer to said two image pickup elements than are said two first objective lenses, for converting said left-hand and said right-hand optical axes to optical axes which are respectively angled inwardly to the left and right.

6. A stereoscopic-vision endoscope system according to claim 5, wherein said two second objective lenses are disposed eccentrically to the right and the left of said left-hand and said right-hand optical axes, respectively and wherein said two image pickup elements are disposed at positions for detecting said two images respectively formed by said two second objective lenses.

7. A stereoscopic-vision endoscope system according to claim 1, wherein said image-signal conversion means generates two image signals for being displayed on said display means from said two image signals, and outputs alternately said two image signals as said stereo image signal.

8. A stereoscopic-vision endoscope system according to claim 5, wherein said image correction means is disposed between said image-signal conversion means and said display means, to independently correct said two image signals which are outputted alternately from said image-signal conversion means.

9. A stereoscopic-vision endoscope system according to claim 1, wherein said two image pickup elements are mounted in a single package.

10. A stereoscopic-vision endoscope system according to claim 9, further comprising a transparent member for sealing said two image pickup elements, wherein said transparent member is a low-pass filter.

11. A stereoscopic-vision endoscope system according to claim 10, wherein said transparent member is a color-temperature correction filter.

12. A stereoscopic-vision endoscope system according to claim 1, further comprising a light shielding plate located between said two image pickup elements.

13. A stereoscopic-vision endoscope system according to claim 1, wherein said image correction means comprises memory means for storing correction information for correcting at least one of magnitude, aberration distortion, inclination and positional shift of said two images, and wherein said image correction means refers to said correction information to process image correction.

14. A stereoscopic-vision endoscope system according to claim 13, wherein said memory means is provided within said endoscope for stereoscopic vision.

15. A stereoscopic-vision endoscope system according to claim 1, wherein said objective optical system is formed by a pair of objective lens systems which are disposed in spaced relation in left-hand and right-hand directions which are perpendicular to a longitudinal axis of said insertion part.

16. A stereoscopic-vision endoscope system according to claim 1, wherein said objective optical system includes two objective lens systems disposed in the forward end of said insertion part, an image transmission optical system for transmitting two images respectively formed by said two objective lens systems, and two image-formation lens systems for respectively imaging the two images which are transmitted through said image transmission optical system, wherein said two image pickup elements are disposed respectively at positions for detecting said two images respectively formed by said two image-formation lens systems.

17. A stereoscopic-vision endoscope system according to claim 16, wherein said insertion part of said endoscope having said two objective lens systems and said image transmission optical system is separable from said proximal part of said endoscope having said two image pickup elements and said two image-formation lens systems.

18. A stereoscopic-vision endoscope system according to claim 17, wherein said insertion part has first memory means for storing information for electrically correcting an image due to said two objective lens systems and said image transmission optical system, and wherein said grasped part has said two image pickup elements and second memory means for storing information for electrically correcting an image due to said two image-formation lens systems.

19. A stereoscopic-vision endoscope system according to claim 1, wherein said objective optical system comprises two objective lenses disposed in parallel to each other, and wherein said image correction means for correcting images such that two images obtained by said two objective lenses are substantially identical to each other in at least one of a magnitude, a distortion, an inclination and a position.

20. A stereoscopic-vision endoscope system comprising:

an endoscope for stereoscopic vision having an elongated insertion part, an output means for outputting illumination light for illuminating an object from an illumination window which is provided in a forward end of said insertion part, an objective optical system provided in the forward end of said insertion part for focusing two images having a parallax with respect to said object which is illuminated by said illumination light, and two image pickup elements for photoelectrically converting said two images at least on the basis of said objective optical system;

image-signal conversion means for converting two image signals photoelectrically converted by said two image pickup elements to a stereo image signal for stereoscopic viewing;

display means for displaying said stereo image signal so as to be recognizable by an observer as a stereoscopic image, and image correction means for electrically correcting at least one of magnitude, inclination and a positional shift of image, together with aberration distortion due to said objective optical system, with respect to the two image signals corresponding to said two images of said stereo image signal, independently of each other in real time.

21. A stereoscopic-vision endoscope system comprising:

an endoscope for stereoscopic vision having an elongated insertion part, an output means for outputting illumination light which illuminates an object from an illumination window which is provided in a forward end of said insertion part, an objective optical system provided in the forward end of said insertion part for focusing two images having a parallax with respect to said object which is illuminated by said illumination light, and two image pickup elements for photoelectrically converting said two images at least on the basis of said objective optical system;

image-signal conversion means for converting two image signals photoelectrically converted by said two image pickup elements to a stereo image signal for stereoscopic viewing;

display means for displaying a stereo image signal so as to be recognizable by an observer as a stereoscopic image, and first image correction means for electrically correcting relative variation of said two images, and second image correction means for electrically correcting factors deteriorating an image quality, which are included respectively in said two images, independently of each other in real time, with respect to the two image signals corresponding respectively to said two images of said stereo image signal.

22. A stereoscopic-vision endoscope system according to claim 21, wherein said second image correction means corrects aberration distortion.

* * * * *